US009265870B2

(12) United States Patent
Reichenbach et al.

(10) Patent No.: US 9,265,870 B2
(45) Date of Patent: Feb. 23, 2016

(54) PUMPING BLOOD

(75) Inventors: Steven H. Reichenbach, Pleasanton, CA (US); Pieter W. C. J. le Blanc, Rancho Cordova, CA (US); Yi-Ren Woo, Livermore, CA (US); David Gary Eldridge, Dublin, CA (US); Stephen G. Briana, Pleasanton, CA (US); William V. Hodges, Tracy, CA (US); Eric Lee, Oakland, CA (US)

(73) Assignee: THORATEC CORPORATION, Pleasanton, CA (US)

( * ) Notice: Subject to any disclaimer, the term of this patent is extended or adjusted under 35 U.S.C. 154(b) by 262 days.

(21) Appl. No.: 13/273,185

(22) Filed: Oct. 13, 2011

(65) Prior Publication Data

US 2012/0095281 A1 Apr. 19, 2012

Related U.S. Application Data

(60) Provisional application No. 61/392,811, filed on Oct. 13, 2010, provisional application No. 61/393,241, filed on Oct. 14, 2010.

(51) Int. Cl.
  *A61M 1/10* (2006.01)
  *A61M 1/12* (2006.01)
(52) U.S. Cl.
  CPC .............. *A61M 1/101* (2013.01); *A61M 1/122* (2014.02); *A61M 1/12* (2013.01)
(58) Field of Classification Search
  CPC ..... A61M 1/10; A61M 1/101; A61M 1/1031; A61M 1/1036
  USPC ............................. 600/16; 623/3.1, 3.13, 3.14
  See application file for complete search history.

(56) References Cited

U.S. PATENT DOCUMENTS

| | | | |
|---|---|---|---|
| 4,082,376 A | 4/1978 | Wehde et al. |
| 4,458,366 A | 7/1984 | MacGregor |
| 4,625,712 A | 12/1986 | Wampler |
| 4,688,998 A | 8/1987 | Olsen et al. |
| 4,704,121 A | 11/1987 | Moise |
| 4,779,614 A | 10/1988 | Moise |
| 4,817,586 A | 4/1989 | Wampler |
| 4,846,152 A | 7/1989 | Wampler et al. |
| 4,895,557 A | 1/1990 | Moise et al. |

(Continued)

FOREIGN PATENT DOCUMENTS

| | | |
|---|---|---|
| AU | 2 627 366 A1 | 5/2013 |
| CA | 2624704 A1 | 4/2007 |

(Continued)

OTHER PUBLICATIONS

PCT Invitation to Pay Additional Fees for Application No. PCT/US2011/056217 dated Jan. 25, 2012, 5 pages.

(Continued)

*Primary Examiner* — Joseph Dietrich
(74) *Attorney, Agent, or Firm* — Kilpatrick Townsend & Stockton LLP

(57) ABSTRACT

A blood pump includes a rotor having a flared portion downstream proximate a downstream bearing that supports the rotor. The flared portion of the rotor includes a width greater than a width of an upstream portion of the rotor. A blood pump also includes a housing having an internal wall with a flared portion downstream of a motor stator and proximate a transverse outlet.

44 Claims, 13 Drawing Sheets

(56) References Cited

U.S. PATENT DOCUMENTS

| | | |
|---|---|---|
| 4,906,229 A | 3/1990 | Wampler |
| 4,908,012 A | 3/1990 | Moise et al. |
| 4,944,722 A | 7/1990 | Carriker et al. |
| 4,994,078 A | 2/1991 | Jarvik |
| 5,106,273 A | 4/1992 | Lemarquand et al. |
| 5,393,207 A | 2/1995 | Maher et al. |
| 5,443,503 A | 8/1995 | Yamane |
| 5,588,812 A | 12/1996 | Taylor et al. |
| 5,613,935 A | 3/1997 | Jarvik |
| 5,695,471 A | 12/1997 | Wampler |
| 5,707,218 A | 1/1998 | Maher et al. |
| 5,749,855 A | 5/1998 | Reitan |
| 5,824,070 A | 10/1998 | Jarvik |
| 5,888,242 A | 3/1999 | Antaki et al. |
| 5,917,297 A | 6/1999 | Gerster et al. |
| 5,947,892 A * | 9/1999 | Benkowski et al. ............ 600/16 |
| 5,951,263 A | 9/1999 | Taylor et al. |
| 6,018,208 A | 1/2000 | Maher et al. |
| 6,050,975 A | 4/2000 | Poirier |
| 6,066,086 A | 5/2000 | Antaki et al. |
| 6,123,659 A | 9/2000 | le et al. |
| 6,135,710 A | 10/2000 | Araki et al. |
| 6,149,683 A | 11/2000 | Lancisi et al. |
| 6,186,665 B1 | 2/2001 | Maher et al. |
| 6,227,820 B1 | 5/2001 | Jarvik |
| 6,234,772 B1 | 5/2001 | Wampler et al. |
| 6,278,251 B1 | 8/2001 | Schöb |
| 6,293,901 B1 | 9/2001 | Prem |
| 6,447,266 B2 | 9/2002 | Antaki et al. |
| 6,688,861 B2 | 2/2004 | Wampler |
| 6,692,318 B2 | 2/2004 | McBride |
| 6,991,595 B2 | 1/2006 | Burke et al. |
| 7,070,398 B2 | 7/2006 | Olsen et al. |
| 7,229,258 B2 | 6/2007 | Wood et al. |
| 7,563,225 B2 | 7/2009 | Sugiura |
| 7,575,423 B2 | 8/2009 | Wampler |
| 7,682,301 B2 | 3/2010 | Wampler et al. |
| 7,699,586 B2 | 4/2010 | LaRose et al. |
| 7,699,588 B2 | 4/2010 | Mendler |
| 7,753,645 B2 | 7/2010 | Wampler et al. |
| 7,798,952 B2 | 9/2010 | Tansley et al. |
| 7,802,966 B2 | 9/2010 | Wampler et al. |
| 7,824,358 B2 | 11/2010 | Cotter et al. |
| 7,841,976 B2 | 11/2010 | McBride et al. |
| 7,850,594 B2 | 12/2010 | Sutton et al. |
| 7,862,501 B2 | 1/2011 | Woodard |
| 7,927,068 B2 | 4/2011 | McBride et al. |
| 7,959,551 B2 | 6/2011 | Jarvik |
| 7,963,905 B2 | 6/2011 | Salmonsen et al. |
| 7,976,271 B2 | 7/2011 | LaRose et al. |
| 7,988,728 B2 | 8/2011 | Ayre |
| 7,993,260 B2 | 8/2011 | Bolling |
| 8,002,518 B2 | 8/2011 | Woodard et al. |
| 8,096,935 B2 | 1/2012 | Sutton et al. |
| 8,118,723 B2 | 2/2012 | Richardson et al. |
| 8,118,724 B2 | 2/2012 | Wampler et al. |
| 8,152,845 B2 | 4/2012 | Bourque |
| 8,177,703 B2 | 5/2012 | Smith et al. |
| 8,282,359 B2 | 10/2012 | Ayre et al. |
| 8,343,028 B2 | 1/2013 | Gregoric et al. |
| 8,353,686 B2 | 1/2013 | Cook |
| 8,366,381 B2 | 2/2013 | Woodard et al. |
| 8,366,599 B2 | 2/2013 | Tansley et al. |
| 8,376,707 B2 | 2/2013 | McBride et al. |
| 2002/0147495 A1 | 10/2002 | Petroff |
| 2003/0100816 A1 | 5/2003 | Siess |
| 2004/0236420 A1 | 11/2004 | Yamane et al. |
| 2005/0095151 A1 | 5/2005 | Wampler et al. |
| 2005/0107657 A1 | 5/2005 | Carrier et al. |
| 2005/0254976 A1 | 11/2005 | Carrier et al. |
| 2007/0078293 A1 | 4/2007 | Shambaugh et al. |
| 2007/0156006 A1 | 7/2007 | Smith et al. |
| 2008/0269880 A1 | 10/2008 | Jarvik |
| 2009/0118567 A1 | 5/2009 | Siess |
| 2010/0069847 A1 | 3/2010 | LaRose et al. |
| 2010/0145133 A1 | 6/2010 | Bolling |
| 2011/0144413 A1 | 6/2011 | Foster |
| 2012/0134793 A1 | 5/2012 | Wu et al. |
| 2012/0134832 A1 | 5/2012 | Wu |
| 2012/0253103 A1 | 10/2012 | Robert |
| 2012/0310036 A1 | 12/2012 | Peters et al. |
| 2013/0096364 A1 | 4/2013 | Reichenbach et al. |

FOREIGN PATENT DOCUMENTS

| | | |
|---|---|---|
| CN | 101282748 A | 10/2008 |
| DE | 19854724 A1 | 5/1999 |
| EP | 150320 A1 | 8/1985 |
| JP | 2009511802 A | 3/2009 |
| KR | 2008056754 A | 6/2008 |
| TW | 201221161 A1 | 6/2012 |
| WO | WO0043054 A2 | 7/2000 |
| WO | WO2007040663 A1 | 4/2007 |
| WO | WO2008152425 A1 | 12/2008 |
| WO | WO 2012/051454 A1 | 4/2012 |
| WO | WO 2013/056131 A1 | 4/2013 |

OTHER PUBLICATIONS

PCT Notification of Transmittal of the International Search Report and the Written Opinion for Application No. PCT/US2011/056217 dated May 31, 2012, 19 pages.

PCT Notification of Transmittal of the International Search Report and the Written Opinion for International Application No. PCT/US2012/060071 dated Mar. 27, 2013, 14 pages.

Patent Examination Report No. 1 for corresponding Australian Patent Application No. 2011315969 issued on Dec. 24, 2013, 4 pages.

* cited by examiner

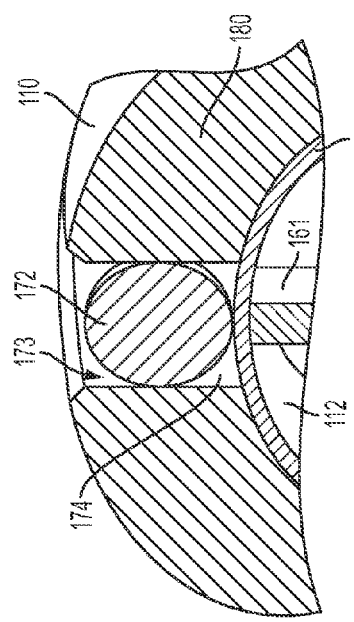
FIG. 5B
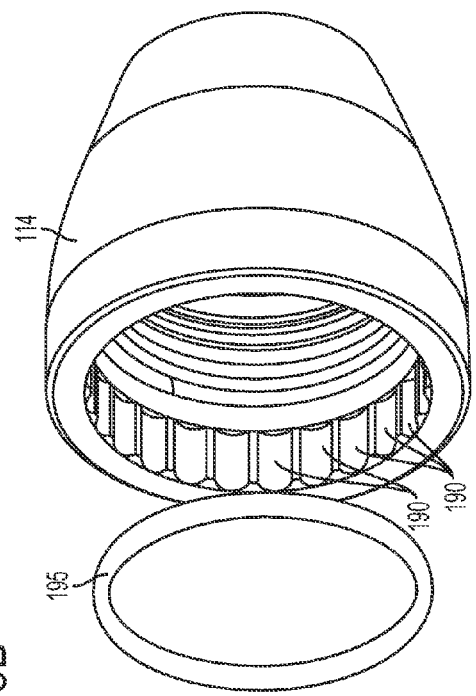
FIG. 5C
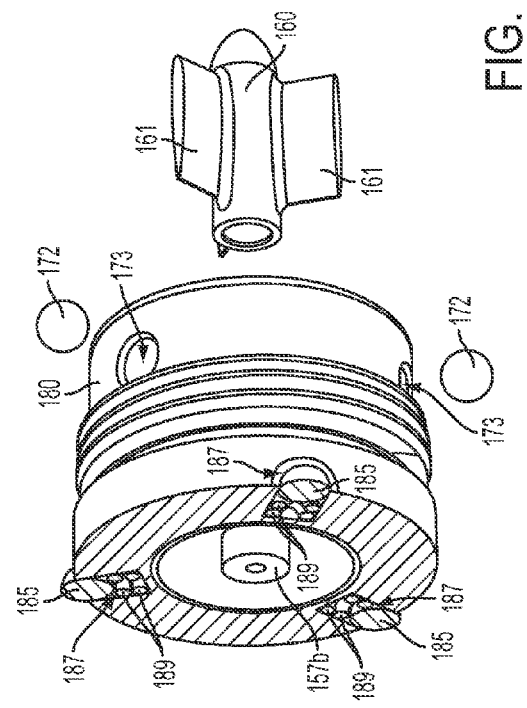

PUMPING BLOOD

CROSS-REFERENCE TO RELATED APPLICATIONS

This application claims priority to and the full benefit of U.S. Provisional Application Ser. No. 61/392,811, filed Oct. 13, 2010, and titled "Pumping Blood," and U.S. Provisional Application Ser. No. 61/393,241, filed Oct. 14, 2010, and titled "Pumping Blood," the entire contents of which are incorporated herein for all purposes by reference.

FIELD

This description relates to pumping blood.

BACKGROUND

Ventricular assist devices, known as VADs, are types of blood pumps used for both short-term and long-term applications where a patient's heart is incapable of providing adequate circulation. For example, a patient suffering from heart failure may use a VAD while the patient awaits a heart transplant. In another example, a patient may use a VAD while the patient recovers from heart surgery. Some heart failure patients may have the device implanted for permanent use. Thus, a VAD can supplement a weak heart or can effectively replace the natural heart's function. VADs can be implanted in the patient's body and powered by an electrical power source outside the patient's body.

SUMMARY

In one general aspect, a device includes a hub having an axis of rotation and a generally cylindrical upstream portion and a downstream portion arranged along the axis of rotation of the hub, the hub including a magnetic material, and blades disposed on the hub, the downstream portion of the hub having an outer dimension that increases in a downstream direction.

Implementations of any of the aspects can include one or more of the following features. For example, the device further includes an upstream bearing component carried on the upstream portion of the hub and a downstream bearing component carried on the downstream portion of the hub, the downstream bearing component having a width greater than a width of the upstream bearing component. The blades are only disposed upstream of the downstream portion of the hub. The downstream portion of the hub has a tapered downstream end. The tapered downstream end has a rounded surface. The device further includes a mixing element on the tapered downstream end. The device further includes a housing defining an inlet, an outlet, and a flow path from the inlet to the outlet, and a motor stator disposed within the housing. The housing includes an internal wall defining the flow path, the internal wall having a width proximate the downstream portion of hub that is greater than a width of the internal wall proximate the upstream portion of the hub. The device further includes stator blades disposed within the flow path proximate the upstream portion of the hub, the stator blades including an upstream bearing component for supporting the upstream portion of the hub. The device further includes a downstream bearing component mounted in the internal wall proximate the downstream portion of the hub for supporting the downstream portion of the hub. The outlet is oriented off the axis of rotation of the hub. The internal wall includes a contoured portion proximate the downstream bearing component. The outer dimension is an outer diameter or a cross-sectional dimension. The hub is coupled at a downstream end of the housing. The housing defines an internal wall having a shape that corresponds to the shape of the downstream portion of the hub. The housing is configured to attach to either an inflow cap or an outflow conduit. Along the axis of rotation, the downstream portion includes a rounded portion that increases to a widest diameter of the hub. The downstream portion includes a second rounded portion that decreases between the widest diameter and the diameter of a downstream bearing component. The housing is configured to direct an axial flow to an outlet oriented transverse to the axis of rotation of the hub.

In another general aspect, a blood pump includes a housing, the housing having an internal wall defining an inlet, an outlet, and a flow path from the inlet to the outlet; the flow path defining a first generally cylindrical volume proximate the inlet, and a second flared volume located downstream of the first generally cylindrical volume, the first generally cylindrical volume having a first width and the second flared volume having an increasing width greater than the first width, a motor stator disposed within the housing, and a motor rotor disposed within the flow path, the motor rotor having a hub, an axis of rotation of the hub, blades for pumping blood, and a magnetic material for electromagnetic rotation of the motor rotor.

Implementations of any of the aspects can include one or more of the following features. For example, the hub includes a generally cylindrical upstream portion and a flared downstream portion, the flared downstream portion having a width greater than a width of the generally cylindrical upstream portion. The blood pump further includes a downstream bearing having a first bearing component mounted in the internal wall and a second bearing component carried by the flared downstream portion of the hub. The internal wall includes a contoured portion proximate the first bearing component. The housing includes a removable portion proximate the first bearing component, the removable portion configured to allow removal of the first bearing component. The blood pump further includes an upstream bearing having a third bearing component carried by an upstream end portion of the hub and a fourth bearing component carried by a bearing stator disposed within the flow path. A position of the bearing stator along the axis of rotation is variable. The downstream bearing has a diameter that is greater than a diameter of the upstream bearing. The housing further includes an inlet cap defining the inlet, the inlet cap being configured to mate to the generally cylindrical portion. The housing further includes a mechanism for limiting removal of the inlet cap. The outlet is oriented off the axis of rotation of the hub. The outlet is oriented transverse to the axis of rotation of the hub.

In another general aspect, a method for pumping blood includes imparting kinetic energy to blood within a first portion of a blood flow path to increase blood flow velocity in the blood flow path, the blood flow path defined by a rotor hub and a wall, directing the blood to a second portion of the blood flow path having a greater width than a width of the first portion of the blood flow path, and converting kinetic energy of the blood to fluid pressure in the second portion of the blood flow path.

Implementations of any of the aspects can include one or more of the following features. For example, the method further includes limiting separation of the blood flow from a surface of the rotor hub in the second portion of the blood flow path. The method further includes limiting recirculation within the blood flow downstream of the second portion of the blood flow path. Imparting kinetic energy includes increasing an axial velocity and a circumferential velocity of the blood within the first portion of the blood flow path. Converting includes reducing a circumferential velocity and/or axial velocity of the blood.

In another general aspect, a blood pump includes a rotor having blades configured to generate a circumferential flow and a downstream portion configured to decrease a circumferential velocity of the circumferential flow. The blood pump includes a housing defining a flow path, the housing being configured to convert the circumferential flow to fluid pressure at an outlet.

Implementations of any of the aspects can include one or more of the following features. For example, the housing is configured to convert the circumferential flow to fluid pressure without stator blades located downstream of the blades of the rotor. The downstream portion is dimensioned to decrease the circumferential flow along an axis of rotation of the rotor, the downstream portion being located on the rotor downstream of the blades. A bearing component is disposed between the rotor and the housing, and the downstream portion is dimensioned to control flow separation within the flow path to control washing of the bearing. The downstream portion includes a flared portion having a cross-sectional dimension that increases along a downstream dimension. The housing includes a flared portion located about the flared portion of the rotor, such that an inner cross-sectional dimension of the housing increases along the downstream dimension. A distance between the flared portion of the rotor and the flared portion of the housing is substantially consistent along the axis of rotation. The housing includes a wall oriented to direct flow transverse to an axis of rotation of the rotor, the wall including a bearing component configured to engage the rotor.

In another general aspect, a blood pump includes a housing defining an inlet, an outlet, and a flow path between the inlet and the outlet. A rotor is mechanically suspended in the housing and is located within the flow path. The rotor has an axis of rotation and blades configured to produce an axial flow about the rotor along the axis of rotation. The housing is configured to direct the axial flow to the outlet in a direction off the axis of rotation.

Implementations of any of the aspects can include one or more of the following features. For example, the housing is configured to direct the axial flow to the outlet in a direction transverse to the axis of rotation. The housing is configured to direct the axial flow to the outlet without stator blades downstream of the rotor. A portion of the housing that directs the axial flow transverse to the axis of rotation is located downstream of the blades of the rotor. The portion of the housing includes an internal wall oriented orthogonal to the axis of rotation. A downstream bearing component for supporting the rotor is disposed on the internal wall.

In another general aspect, a device includes a hub that has an axis of rotation and a midpoint along the axis of rotation. The hub has a downstream portion and an upstream portion arranged along the axis of rotation. Blades are disposed on the upstream portion of the hub. The downstream portion has a flared portion that has an outer diameter that increases along a downstream direction to a greatest outer diameter of the hub, the flared portion being located downstream of the midpoint.

Implementations of any of the aspects can include one or more of the following features. For example, the hub has an end portion that has an outer diameter that decreases along the downstream direction from the greatest outer diameter of the hub. The flared portion and the end portion are rounded. The outer diameter of the end portion decreases to a diameter of a downstream bearing component. The hub has a central portion between the upstream portion and the flared portion, and the blades terminate upstream of the central portion. The central portion of the hub is substantially cylindrical. The central portion of the hub includes the midpoint. The upstream portion terminates upstream of the midpoint. The blades do not extend beyond the midpoint in the downstream direction. No blades are disposed on the central portion or the downstream portion. The device includes a housing that defines a flared portion about the flared portion of the hub, the flared portion of the housing having an inner diameter that increases in the downstream direction. The housing defines a blood flow path such that no stator blades are located downstream of the hub. A downstream bearing component is attached to a removable downstream portion of the housing. The housing defines an outlet orthogonal to the axis of rotation. An upstream bearing component is attached to a stator located upstream of the hub. The position of the stator relative to the housing is variable to set a bearing gap between the hub and one or more of the upstream bearing component and the downstream bearing component. The housing is configured to attach to any of a plurality of inlet components.

In another general aspect, a graft assembly for connecting a pump outlet portion to tissue includes a woven material that defines a lumen. A reinforcement component is located about the outer circumference of the woven material. A support structure for coupling the woven material to an outlet portion of the pump is molded about an end region of the woven material. The support structure includes a flange configured to be captured by a fitting.

Implementations of any of the aspects can include one or more of the following features. For example, a fitting is slidably positioned over the support structure. The fitting is configured to snap over a raised portion on an outer surface about the pump outlet such that the fitting compresses the flange of the support and forms a hermetic seal about the outlet portion. The fitting is configured to screw over a threaded portion on an outer surface about the pump outlet such that the fitting compresses the flange of the support structure and creates a hermetic seal around the pump outlet. The reinforcement component about the outer circumference of the woven material includes a wire wrapped helically about the outer circumference of the woven material.

In another general aspect, a method of positioning an upstream stator during pump assembly includes placing the upstream stator within an inlet bore of the pump. The method includes compressing a conduit that defines the inlet bore at regions that correspond to blade locations of the upstream stator to anchor the upstream stator and provide sealing about the blades.

Implementations of any of the aspects can include one or more of the following features. For example, compressing the conduit includes placing sealing elements about the conduit at regions corresponding to blade locations of the upstream stator. An outer housing component is fitted over the conduit and the sealing elements such that an inner surface of the outer housing compresses the sealing elements against an outer surface of the conduit.

All of the features described can be used in any combination and subcombination, including combinations across multiple aspects described above. Features described herein with respect to one aspect can additionally or alternatively be included in implementations of any of the other aspects. The details of one or more implementations are set forth in the accompanying drawings and the description below. Other features will be apparent from the description and drawings, and from the claims.

DESCRIPTION OF THE DRAWINGS

FIG. 5B is a cutaway perspective view of a stator and a housing of the blood pump of FIG. 1.

FIG. 5C is an exploded view of the inlet end of the blood pump of FIG. 1.

The details of one or more implementations are set forth in the accompanying drawings and the description below. Other features will be apparent from the description and drawings, and from the claims.

DETAILED DESCRIPTION

Figure 1:
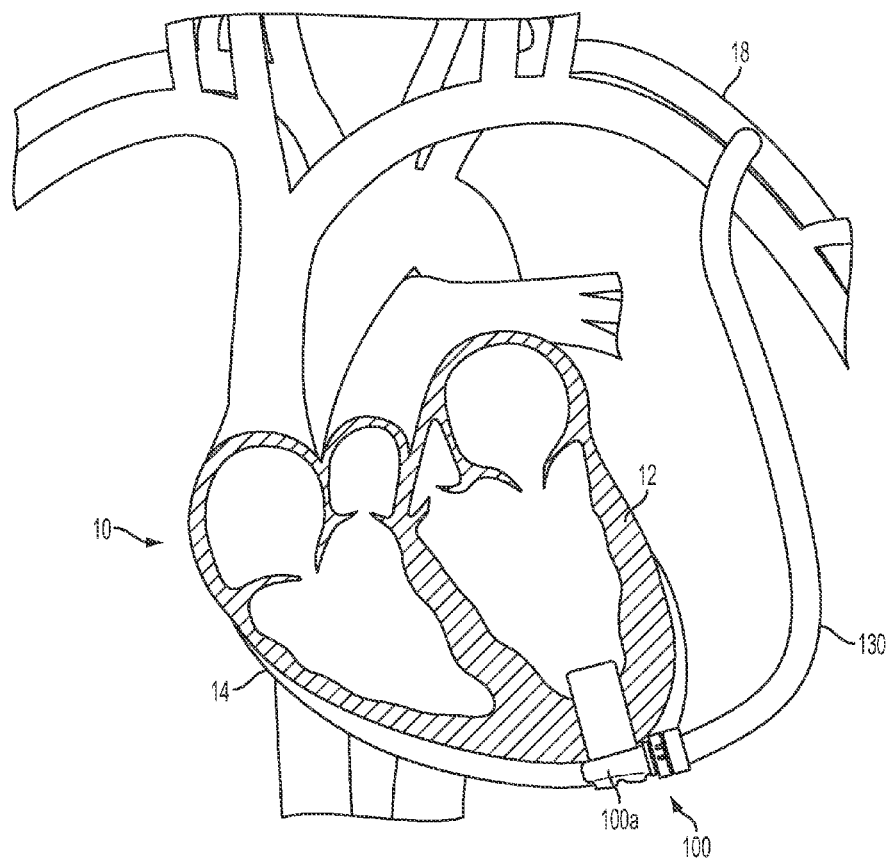
FIG. 1 illustrates a blood pump assembly implanted at a heart.

Referring to FIG. 1, an exemplary blood pump assembly 100 can be implanted in a patient's body to supplement, or in some cases replace, the natural pumping function of a heart 10. The blood pump assembly 100 includes a blood pump 100a, which can be implanted to receive blood from the heart 10, for example, from a left ventricle 12 of the heart 10. As shown, the blood pump 100a pumps blood through an outflow conduit 130 to the patient's circulatory system, for example, to a peripheral artery 18. The blood pump assembly can also be implanted such that the blood pump 100a receives blood from a right ventricle 14 of the heart 10 and supplies blood to, for example, a pulmonary artery. In general, the blood pump assembly 100 can be implanted superficially just below the skin or deep below the rib cage, muscular tissue, and/or organs. Besides the left and right ventricles, blood can be directly obtained from sources such as the left or right atrium, or a peripheral artery or vein. In other words, the pump 100a can be implanted with a conduit fluidly communicating blood from a part of the vasculature that is not the heart to the pump 100a. Similarly, the pump 100a can deliver blood to any part of the vasculature including major arteries, veins, the aorta, or even organs.

Figure 2:
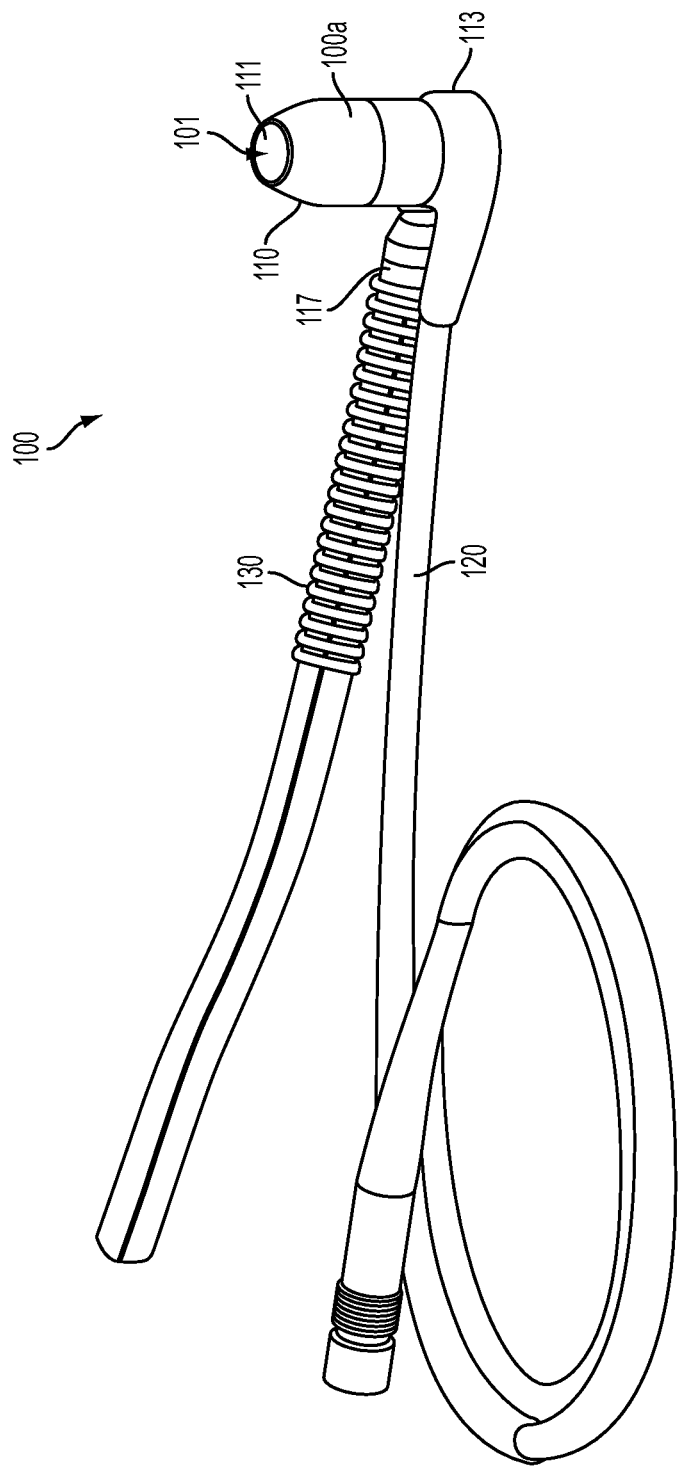
FIG. 2 is a perspective view of the blood pump assembly of FIG. 1.

The exemplary blood pump assembly 100, shown in FIG. 2, includes the blood pump 100a having a housing 110 defining an inlet 101 at a first end 111 and a transverse outlet 103 (FIG. 3) defined by a generally transverse outlet cannula 117 proximate a second end 113. As shown, the flexible outflow conduit 130 is connected to the outlet cannula 117 for returning blood to the patient's circulatory system. The blood pump 100a also includes a cable 120 for connection to a control unit that provides electrical energy to operate the pump 100a. Both the outlet cannula 117 and the cable 120 are disposed proximate a second end 113 such that the pump 100a can be implanted partially within the patient's heart 10.

The blood pump 100a can be used to provide partial support or full support to a left ventricle or a right ventricle. The blood pump 100a can also be used for biventricular support with a second blood pump 100a or a blood pump of another type. The blood pump 100a may also be used to supplement circulatory support by moving blood from a source in a first part of the vasculature, for example, an artery or vein such as the subclavian artery, and pumping it into another part of the vasculature, such as the aorta.

Figure 3:
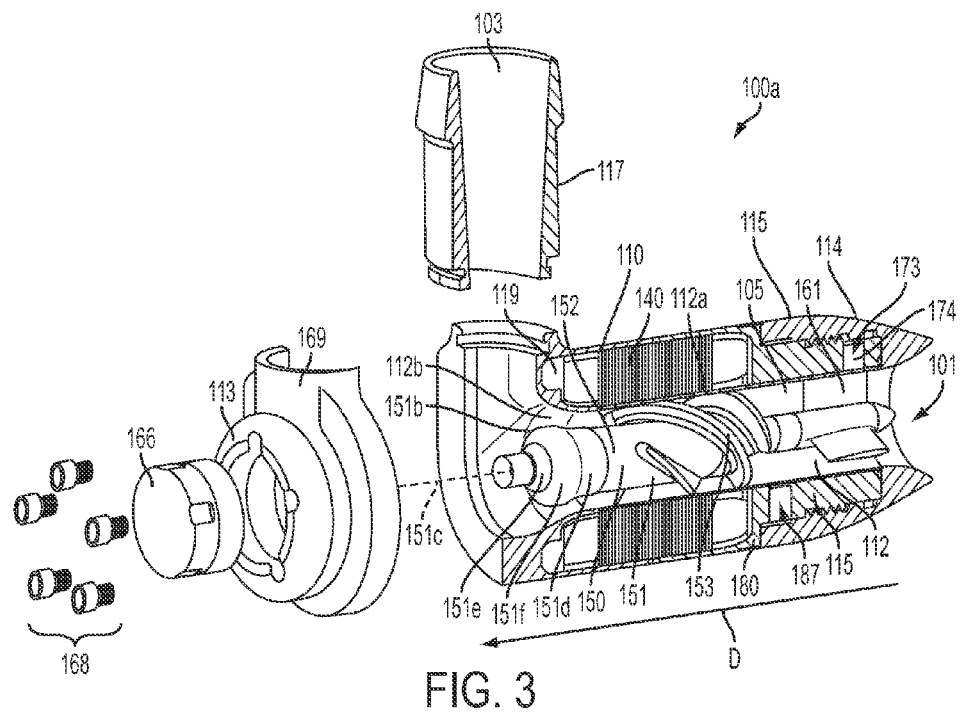
FIG. 3 is an exploded partial cross-sectional perspective view of the blood pump of FIG. 1.
Figure 4:
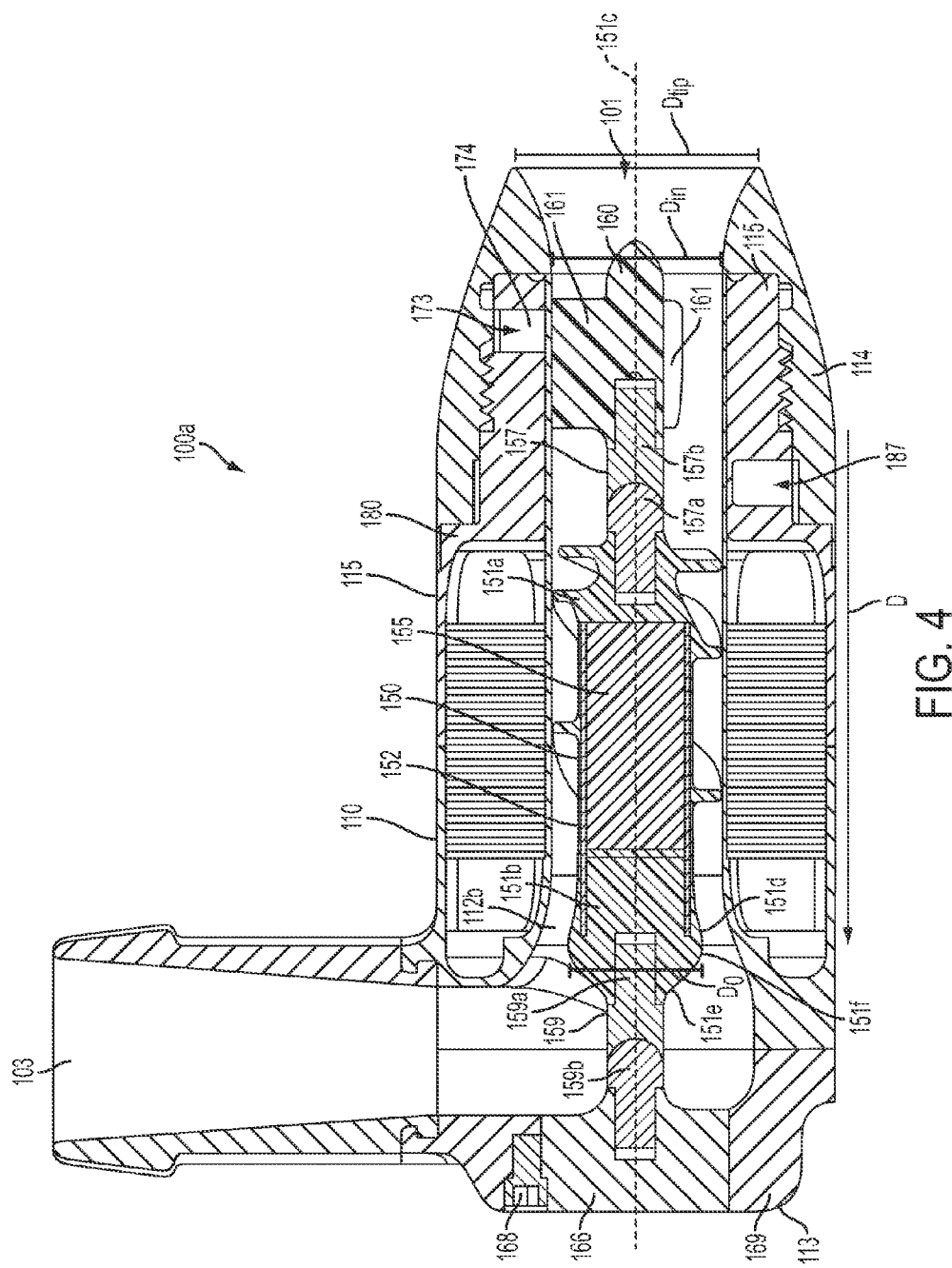
FIG. 4 is a cross-sectional view of the blood pump of FIG. 1.

As shown in FIGS. 3 and 4, the blood pump 100a includes a motor stator 140 and a motor rotor 150 that operate to pump blood through the blood flow path 105. The motor stator 140 is disposed within a recess 119 of the housing 110 and is sealed from the blood flow path 105 and an external environment. The motor stator 140 generates a magnetic field to drive a magnetic material embedded inside the motor rotor 150 to rotate and result in the action of pumping blood. The motor rotor 150 includes a hub 151 and impeller blades 153. In various implementations, the motor rotor 150 includes in whole or in part a magnet 155. Suitable magnetic materials include, but are not limited to, a permanent magnet (for example, a ferromagnetic material such as iron or nickel).

The exemplary hub 151 is supported within the blood flow path 105 by an upstream bearing assembly 157 and a downstream bearing assembly 159 housed within a body of the outlet cannula 117. The hub 151 can generally be divided into three sections: an upstream portion 151a that includes the impeller blades 153, a central or mid-distal portion 152 without impeller blades, and a distal or downstream end portion 151b having flared region 151d with a width greater than either of or both of the upstream portion 151a and the mid-distal portion 152. In some implementations, the impeller blades 153 begin proximate the upstream bearing assembly 157 at the bearing component on the hub 151 and terminate at about a mid-point along the length of the rotor 150. The termination point of the impeller blades 153 can vary slightly, for example, just before or just after the mid-point of the rotor 150.

The central or mid-distal portion 152 of the hub 151 is located immediately downstream of the blades, between the upstream end portion 151a and the downstream end portion 151b. The rotor 150 has no blades on the central or mid-distal portion 152. The central or mid-distal portion 152 is generally of the same diameter as the upstream end portion 151a of the hub 151. The central or mid-distal portion 152 is a featureless region that covers approximately a total of approximately one quarter or about three eighths of the entire length of the rotor 150, if the rotor 150 includes a flared region 151d. If there is no flared region 151d on the rotor 150, this featureless region will extend for the remaining length of the rotor 150 to the downstream bearing assembly 159. The flared region 151d of the rotor 150 generally covers approximately about one-eighth to about one-quarter of the entire length of the rotor 150.

The upstream bearing assembly 157 includes a ball component 157a carried by an upstream portion 151a of the hub 151 and a cup component 157b carried by a stator 160. Arrangement of the ball and cup components 157a, 157b can be reversed such that the ball component 157a is carried by the stator 160 and the cup component 157b is carried by the upstream portion 151a of the hub 151. The exemplary stator 160 has at least three stator blades 161 for affecting blood flow through the blood flow path 105. For example, the stator blades 161 can be configured to straighten the blood flow entering the inlet 101 before the blood flow comes into contact with the rotor 150 (or the impeller blades 153 on the rotor 150). The stator 160 can be attached to an internal wall 112 at any of a variety of positions by a press-fit spherical structure (not shown). The spherical structures can be inserted through an outer surface of the housing 110 radially inward towards the axis of rotation 151c that runs along the center of the pump 100a. In particular, the axial position of the stator 160 relative to the rotor 150 can be varied in a direction along the axis of rotation 151c to control the distance of the bearing gap between the ball component 157a and the cup component 157b of the upstream bearing assembly 157. This indirectly provides an ability to vary the distance of the bearing gap between a ball component 159b and a cup component 159a of the downstream bearing assembly 159.

As described further below, a spherical structure, which can be made from any material and not just metal, can be used to provide a hermetic seal, for example, completely sealing compartments of the housing 110 to disallow leakage. The spherical structure can be hard so that when press-fitted into the housing 110, friction locks the position of the stator 160 and creates the hermetic seal. In some implementations, because a hermetic seal can be difficult to achieve with a helical thread, set screws are not used to secure the stator 160.

Figure 5A:
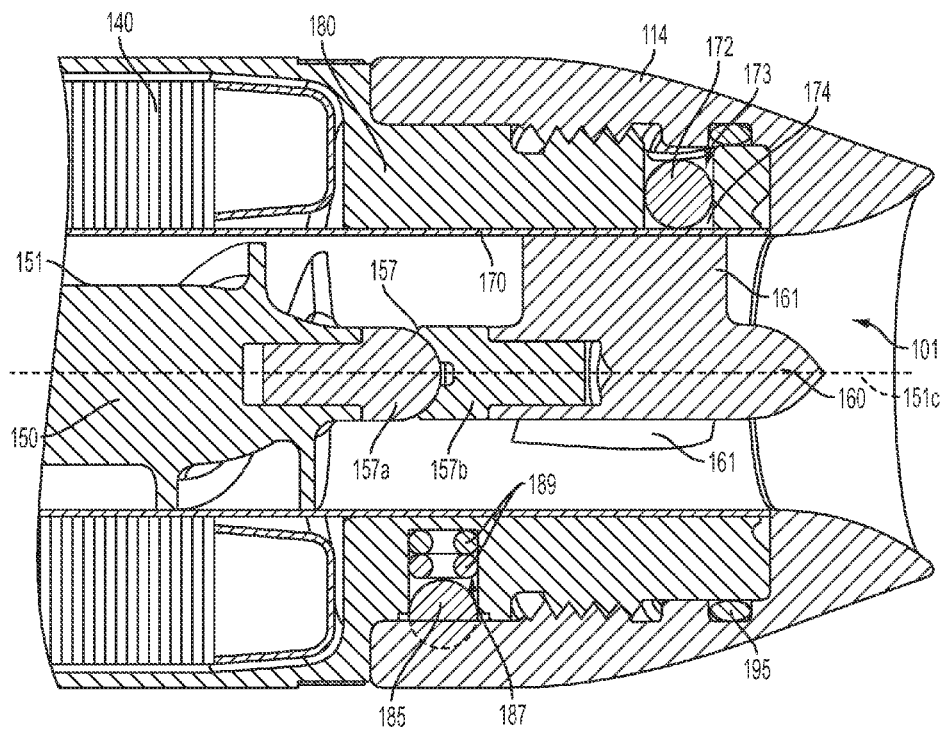
FIG. 5A is a cross-sectional view of an inlet end of the blood pump of FIG. 1.

Referring to FIGS. 5A and 5B, during assembly of the pump 100a, the stator 160 is positioned within a tubular portion 170 of the housing 110. To secure the stator 160, the tubular portion 170 or conduit, which is part of the inner wall 112 of the housing 110, is compressed at regions that correspond to blade locations of the stator 160. Compression of the tubular portion 170 is achieved by inserting sealing elements 172 into plug holes 173 defined through a housing component 180 that is located about the tubular portion 170. The sealing elements 172 reside in the plug holes 173 and directly engage the tubular portion 170 to exert a radial inward force on the tubular portion 170. Each sealing element 172 can be of spherical or hemi-spherical shape. Alternatively, each sealing element 172 can be another object that can both (i) create a seal between the sealing element 172 and a circumferential wall 174 that defines the plug hole 173 (e.g., leaving no gap between the edge of the sealing element 172 and the circumferential wall 174), and (ii) exert a force against the stator blade 161 or another portion of the stator 160 to secure the stator 160 in place.

The positions of the plug holes 173 correspond to locations of the stator blades 161. For example, the plug holes 173 are defined over regions of the tubular portion 170 that engage the ends of the stator blades 161 (FIG. 5B). An inlet cap, such as inlet cap 114, is threaded over the housing component 180. The sealing elements 172 are press-fit by force into the plug holes 173. Friction between the sealing elements 172 and the circumferential walls 174 that define the plug holes 173 helps to secure the sealing elements 172 against the tubular portion 170, which in turn secures the upstream stator 160 by pressing against the stator blades 161. In addition to providing a radial inward force for securing the stator 160, the sealing elements 172 can hermetically seal the plug holes 173 by, for example, expanding slightly when pressed against the tubular portion 170. The sealing elements 172 can be made from any fluid-impermeable material and can be in the form of, for example, spherical plugs. Alternatively, the sealing elements 172 can include cylindrical, hemispherical, or other geometries. Additional seals, such as an o-ring 195, can also be used to seal the housing 110 at other locations.

Referring to FIG. 4, the downstream bearing assembly 159 is anchored at the downstream second end 113 of the housing 110. The exemplary downstream bearing assembly 159 is coupled within the housing 110 at the downstream end 113 just before the blood flow path 105 bends into the outlet 103. The downstream bearing 159 includes the cup component 159a, carried by the downstream portion 151b of the hub 151, and the ball component 159b, carried by a plug 166. Similarly, the components of the downstream bearing assembly 159 can be reversed such that the cup component 159a is carried by the plug 166 and the ball component 159b is carried by the downstream portion 151b of the hub 151. As the rotor hub 151 rotates, the cup component 159a and the ball component 157a on the hub 151 rotate relative to the ball component 159b and the cup component 157b, which remain stationary relative to the housing 110.

By contrast with other pumps in which an aft stator or diffuser is located downstream of a rotor to axially straighten the flow downstream of a downstream bearing assembly, the exemplary pump 100a locates the ball and cup bearing assembly 159 at a terminal point of the blood flow in the axial direction, with the bearing assembly 159 coupled directly at the most distal or downstream inner surface at end 113 of the housing 110. In other words, in the pump 100a, no blood flows in an axial direction downstream of the downstream bearing assembly 159. Instead, blood flows transversely away from the downstream bearing assembly 159 into and through the outlet 103.

With the rotor 150 mechanically suspended in the housing 110 as shown in FIG. 4, the downstream end portion 151b of the rotor 150 is not mounted on a circumferential wall of the pump 100a. In other words, the cup component 159a of the rotor 150 is not supported by any annular internal wall of the housing 110, whether through direct engagement or through another component. Rather, the downstream end portion 151b is supported at the distal-most end 113 of the pump 100a by the ball component 159b.

The plug 166 at the aft end of the pump 100a is removable and is secured by a plurality of screws 168 or by another fastening mechanism. The plug 166 is secured to an end cap 169. The engagement of the plug 166 to the end cap 169 secures the aft ball and cup bearing assembly against the rotor 150. It is designed to allow for easy assembly of the motor stator 140 as well as the rotor 150 of the pump. In combination with the mechanism for securing the stator 160 shown in FIGS. 5A and 5B, gap clearance in the ball and cup assemblies of both the fore and aft bearings 157, 159 can be precisely measured and varied. As shown, the plug 166 and the end cap 169 can include a portion of the internal wall 112 that defines the blood flow path 105 through the pump 100a. As an alternative to the plug 166, the aft portion of the housing 110 can be a single removable component that includes the geometry of the plug 166 and attaches to the forward portion of the housing 110. The outflow cannula 117 of the pump 110a can also be fabricated as an integral portion of the housing 110.

The impeller blades 153 are included on the upstream portion 151a of the hub 151 and extend toward the downstream portion 151b. The exemplary impeller blades 153 may have a varying local angle of attack along their length. The exemplary impeller blades 153 generally have a decreasing angle of attack relative to an axis of rotation 151c of the hub 151 from the upstream portion 151a of the hub 151 towards the downstream portion 151b of the hub 151. The exemplary impeller blades 153 terminate before reaching the downstream portion 151b of the hub 151. Specifically, the impeller blades 153 terminate at approximately the mid-point of the rotor 150, measured along the axis of rotation 151c. Thus, the impeller blades 153 impart kinetic energy to the blood to increase blood flow velocity within the blood flow path 105. The varying blade angle of attack or wrap angle of the impeller blades 153 is configured to efficiently increase both axial and circumferential velocities of the blood flow.

In some implementations, a total of three impeller blades 153, each spaced at about 60 degrees apart, begin adjacent at or immediately adjacent the upstream ball component 157*a* of the upstream bearing assembly 157. It should be noted that as few as one blade 153 and as many as ten or more blades 153 can be used. However, three or five blades 153 are generally considered appropriate for a blood pump application. Each of the blades 153 has generally the same width along its entire length. However, if the diameter of the upstream bearing assembly 157 is smaller than the diameter of the hub 151, as in this exemplary case, each blade 153 may be wider at its initial point than at its termination point. In the implementation illustrated, the blades 153 each wrap around the hub 151 of the rotor 150 approximately about 270 degrees. In practice, blades 153 can wrap around the rotor 150 as little as 90 degrees and as much as 300 degrees. Lesser or more turn is possible, but the range of 90 to 300 degrees is considered most appropriate. The width of the blade 153 is directly correlated to the number of blades 153 selected. If more blades 153 are used, a smaller width may be necessary to accommodate all the blades 153 on the rotor 150. The degree of wrap about the rotor 150 and spanning distance of the blades 153 on the rotor 150 can dictate the sharpness of the helical turns of the blades 153.

The exemplary downstream portion 151*b* of the hub 151, referring to the part of the rotor 150 proximate to the downstream ball and cup bearing assembly 159, includes a width that is greater than a width of the upstream portion 151*a*. The upstream portion 151*a* is the part of the rotor 150 extending from the upstream ball and cup bearing assembly 157 to at least a point on the rotor 150 where the blades 153 terminate. With exception of the blades 153, the body of the hub 151 generally has a relatively constant diameter along its entire length. The downstream portion 151*b* of the hub 151, in some implementations, takes on a bulbous or partially spherical shape with an increase in diameter of the hub 151, creating a flared region. In other implementations, a flared region of this downstream portion 151*b* can simply be curvaceous with an increase in width that may taper to a same or lesser width than the upstream portion 151*a* of the hub 151. In still other implementations, the downstream portion 151*b* of a flared region may taper to a diameter larger than the upstream portion 151*a* of the hub 151, but lesser than the largest diameter of the flared region.

For example, the greatest width of the downstream portion 151*b* is greater than the greatest width of the upstream portion 151*a*. In another example, the average width of the downstream portion 151*b* is greater than the average width of the upstream portion 151*a*. In yet another example, a portion of downstream portion has an outer dimension greater than the maximum width of the upstream portion 151*a*. The exemplary downstream portion 151*b* includes a widest portion 151*f* having an outer dimension $D_0$ between a flared portion 151*d* and an end portion 151*e*. The flared portion 151*d* flares outward, having an outer dimension that increases in the downstream direction D. In various implementations, the contour or surface of the flared portion 151*d* is rounded. In various implementations, the contour or surface of the flared portion 151*d* has a serif-like shape. In various implementations, the flared portion has a generally flat surface with a cone-like shape. In various implementations, the contour or surface of the flared portion 151*d* is substantially elliptical.

The outer dimension can be, for example, an outer diameter or a cross-sectional dimension orthogonal to the axis of rotation 151*c* of the hub 151. The outer dimension of the downstream portion 151*b* may increase to the widest portion 151*f* of the hub 151. From the widest portion 151*f*, the exemplary outer dimension decreases over the end portion 151*e* in the downstream direction D. In various implementations, the outer dimension generally increases moving in the axial flow direction D. In various implementations, only a portion of the downstream portion 151*b* has an increasing outer dimension. In various implementations, the outer dimension of the downstream portion 151*b* increases along its entire length. In various implementations, the downstream portion has a substantially bulbous shape. In various implementations, the downstream portion has a substantially parabolic cross-sectional shape.

As shown in FIGS. 3 and 4, the exemplary end portion 151*e* has a spherical curvature downstream of the widest portion 151*f* of the rotor hub 151. However, other symmetric curved shapes can be used for the end portion 151*d*. For example, the end portion 151*d* can be tapered along the axis of rotation 151*c* of the rotor hub 151. The flared portion 151*d* and the end portion 151*e* can each optionally include, for example, a convex, concave, or linear outer contour along the axis of rotation 151*c* of the hub 151.

The rotor hub 151 is located within the blood flow path 105, which is defined as a space between the rotor hub 151 and the inner wall 112 of the housing. The upstream portion 151*a* of the rotor hub 151 is disposed proximate a generally cylindrical portion 112*a* of the housing 110 near the stator assembly 161. The downstream portion 151*b* is disposed proximate a flared portion 112*b* of the housing 110. About the flared portion 151*d* of the hub 151, the exemplary flared portion 112*b* of the internal wall 112 substantially matches the contour of the flared portion 151*d*.

The blood flow path 200 includes a first generally cylindrical volume proximate the inlet 101, defined by the generally cylindrical portion 112*a* of the internal wall 112. The internal wall 112 defines a second flared volume located downstream of the first generally cylindrical volume, defined by the flared portion 112*b*. The first generally cylindrical volume has a first width, and the second flared volume has an increasing width greater than the first width.

In various implementations, the flared portion 112*b* of the housing 110 and the flared portion 151*d* of the hub 151 are dimensioned and configured such that a substantially consistent distance is maintained between the flared portion 151*d* and the flared portion 112*b*. In other implementations, the gap or distance between the flared portion 151*d* and the fared portion 112*b* may be similar but not identical to the gap between the rotor hub 151 and the generally cylindrical portion 112*a*. The exemplary flared portion 112*b* of the internal wall 112 continues to flare outward from the hub 151 along the downstream portion 151*b* of the hub 151. For example, the gap between the flared portion and the corresponding contoured wall has a distance ranging from approximately about 0.03 inches to about 0.09 inches. Some exemplary implementations have a gap distance of approximately 0.06 inches. This gap distance is similar to the distance between the central/mid-distal portion of the hub without impeller blades 153, and the upstream portion of the hub without the blades 153. In some cases, the gap distance between the flared downstream portion 151*d* and the flared portion 112*b* of the contoured wall 112 can be slightly larger or smaller than the distance between the upstream portion of the rotor and the generally cylindrically-shaped wall. Generally, the gap distance between the impeller blades 153 and the inner wall 112 of the housing 110 ranges from approximately about 0.001 inches to about 0.005 inches for minimizing hemolysis and prevent energy loss. Some exemplary implementations have about 0.003 inches of gap distance between the tip of the impeller blade 153 and the inner wall 112 of the housing 110.

This unique configuration of a flared portion 151f on the hub 151 allows kinetic energy of the blood in the form of circumferential velocity to be efficiently converted to static fluid pressure. The arrangement of the outlet cannula 117 transverse to the axis of rotation 151c of the hub 151 allows blood to be pumped through the outlet 103 without downstream stator blades and without redirecting circumferential velocity of the blood to an axial velocity. For example, kinetic energy is imparted to blood within a first portion of the blood flow path 105, defined by the generally cylindrical portion 112a. Blood flow velocity increases within the first portion of the blood flow path 105. Blood is then directed to a second portion of the blood flow path, for example, the portion defined by the flared portion 112b of the housing 110. The second portion of the blood flow path has a greater diameter or width than the greatest width or diameter of the first portion of the blood flow path. Kinetic energy of the blood is then converted to fluid pressure in the second portion of the blood flow path.

The inlet 101 is defined by a separate inlet cap 114 that is threadedly engaged with a main body 115 of the housing 110. The inlet cap 114 is removable from the main body 115, permitting one of several different inlet caps to be selected for use. Because the inlet cap 114 is a modular component, different inlet caps can permit the pump 100a to be used in different applications. Applications may include left ventricular support, right ventricular support, atrial support, peripheral circulatory support, and pediatric circulatory support, which are all aspects of mechanical circulatory support. The inlet cap 114 includes properties selected based on a particular application in which the pump 100a is to be used. For example, the shape, size, material, and texture of the inlet cap 114 can be selected according to a particular implantation location selected for a given patient. The inlet cap 114 or the housing 110 can include exterior structures that attach to, for example, a sewing ring or an inflow conduit. To prevent or limit removal of the inlet cap 114 from the housing 110, a ratchet mechanism or other retaining mechanism can be included.

Referring to FIG. 5C, a ratchet mechanism limits rotational movement of the inlet cap 114 relative to the housing 110. The ratchet mechanism includes limiting elements 185 that engage inner grooves 190 defined in the inner circumference of the inlet cap 114. The limiting elements 185 are partially disposed in radial holes 187 defined partially into the housing 110, for example, in the housing component 180. Unlike the plug holes 173, the radial holes 187 extend only partially through the housing component 180. Resilient elements 189, such as o-rings, are disposed in the holes 187 between the limiting elements 185 and the housing component 180. The resilient elements 189 position the limiting elements 185 such that the limiting elements 185 protrude out of the holes 187. The resilient elements 189 also act as a springs to counteract the radial force exerted by the inlet cap 114 so that the limiting elements 185 are frictionally engaged with the inlet cap 114. Thus, when the inlet cap 114 is connected to the housing component 180, the limiting elements 185 enter and situate in the grooves 190. The resilient elements 189 exert a radial outward force on the limiting elements 185 to limit rotation of the inlet cap 114 relative to the housing component 180. In some implementations, the inlet cap 114 is threadedly screwed onto the housing component 180.

The combination of the grooves 190, the limiting elements 185, and the resilient elements 189 help to provide additional friction so that the inlet cap 114 cannot be easily unscrewed. The limiting elements 185 can each have a spherical structure, or can have another shape that includes an exposed curved surface to engage the grooves 190. Alternately, the combination of limiting elements 185 and resilient elements 189 can be replaced by a spring-loaded plug with a protruding element for engaging the grooves 190. As another alternative, rather than a curved surface at each groove 190 and a rounded limiting element 185, a saw-like or other configuration can be used to generate friction to prevent the inlet cap 114 from coming loose.

The inlet cap 114 shown in FIGS. 2-4 can be used for placement of the inlet 101 of the pump 100a within a left ventricle or a right ventricle. In the example of direct ventricular or atrial cannulation, the inlet 101 of the pump 100a is directly inserted through the wall of the selected ventricle or atrium, with the wall located about the exterior of the pump 100a. One of several interchangeable inlet caps can be selected for patients with different ventricular or atrial dimensions that may be a result of inherent anatomy or from diseases, including, but not limited to, cardiomyopathy that thickens the epicardial wall of the ventricles. For example, an inlet cap with a suitable length can be selected to accommodate a particular heart wall thickness, or to extend a desired distance or depth into a particular chamber of the heart. The inlet cap 114 can also be selected to include a particular outer diameter or a particular type of engagement structure that permits coupling to the heart. In some implementations, as shown in FIG. 4, an inlet, whether designed for direct cannulation into the heart wall or for use with an inflow conduit, may have a larger lumen diameter $D_{tip}$ that tapers from the tip of the inlet to a smaller diameter that is same as the inner diameter $D_{in}$ at the upstream portion of the rotor for blood flow. In other words, the cross-sectional area of the blood flow path decreases as the blood meets the stator blades 161 from the tip of the inlet cap 114. In other implementations where an inflow conduit is used, the inflow conduit can also have a similar tapering lumen at the inlet 101, or have an inlet 101 with a lumen diameter that is same as inner diameter as the upstream portion of the rotor 150 defined by the internal wall 112 and the rotor 150 about the stator blades 161.

In examples of direct cannulation, to attach the pump 100a to the heart, the inlet cap 114 can be coupled to a sewing ring that is sewn to, for example, the apex of the left ventricle. The pump 100a can be positioned to extend into the opening of the sewing ring, and into a hole in the heart located at the opening of the sewing ring. This results in the inlet 101 being located within the heart, with the sewing ring located about the inlet cap 114. In some implementations, the sewing ring can engage exterior structures of the inlet cap 114, securing the pump 100a at a desired position relative to the heart. The exterior structures can include one or more of, for example, channels, notches, grooves, ridges, threads, and detents. As an alternative, the pump 110a can be positioned such that the sewing ring is positioned about the main body 115 of the housing 110 and the sewing ring engages exterior structures of the main body 115.

Instead of directly cannulating the pump 100a into the heart, the pump 100a can be used to supplement blood flow using a source of blood other than the heart. For example, the pump 100a can obtain blood from a source such as a peripheral arterial or venous vessel and can pump the blood into another peripheral arterial or venous vessel, or to an organ. Other inlet configurations are also possible, depending on the type, dimension, and material of inflow conduit used. For instance, a conduit can be integrated with a connector that directly couples to the pump 100a in the place of an inlet cap 114. Many different configurations of an interchangeable integrated conduit and connector that directly couples to the pump 100a in place of the inlet cap 114 are possible. The configurations can vary based on, including, but not limited to, a vessel to which the inflow conduit is attached, the application (e.g., a surgical or percutaneous approach), and the type of attachment to the vessel. In other implementations, there can be one inlet that is designed to be adaptable to different sized or materials of conduits such that the conduits can be interchanged. Nevertheless, it is contemplated that an interchangeable inlet cap can provide the most convenience for a surgeon to use the same pump for different applications that range from different modes of direct cannulation to different modes of non-cannulation. In a non-cannulation implant procedure, the pump 100a can be implanted anywhere in the body, subcutaneously just below a layer of skin or superficial muscular layers, or deep below the rib cage. In these applications, an inflow conduit will draw blood from a source such as an artery, vein, or even a part of the heart such as the atrium (for example, by percutaneous access), through the inlet cap 114 into the pump 100a.

In any of the applications described above, including direct ventricular cannulation or subcutaneous implantation, the pump 100a can also be placed using minimally-invasive techniques. Minimally invasive techniques include intracostal entry, or in the case of a non-cannulation approach, for example, by creating a pocket under the pectoral muscle near the clavicular region. In other implementations, an inflow conduit attached to the inlet cap 114 can be percutaneously inserted. For example, an inflow conduit can be percutaneously inserted into a subclavian vein. The inflow conduit can pass through the superior vena cava into the right atrium of the heart and can penetrate through the septal wall into the left atrium. Blood drawn into the pump 100a can then be pumped through an outflow conduit into a peripheral artery. The pump 100a can be located outside the patient's body, or if implanted, can be subcutaneously or minimally invasively placed within the patient's body according to any description provided above.

As an alternative to the inlet cap 114 of FIGS. 2-4, an inlet cap can have an outer diameter and/or an inner diameter that match corresponding dimensions of the housing 110 such that the inlet cap is generally cylindrical. A uniformly shaped and generally cylindrical inlet cap is suitable for direct cannulation approaches. Inlet caps may have other shapes and/or features for coupling with a sewing ring or for coupling with an interchangeable inflow conduit. Like the housing 110, an inlet cap can be made of titanium. An inlet cap use for direct cannulation can include external and/or internal surfaces that are sintered, beaded, or otherwise textured to promote deposition of cells which will form an endothelial-like layer to minimize thrombus formation or simply to promote tissue growth. In some implementations, an inlet cap having a textured surface that is sintered and beaded on the entire external surface is suitable for direct cannulation or implantation into an organ, such as a ventricle of the heart. In various other implementations, the textured surface on the exterior of the inlet can terminate just before the external surface edge, at the edge, or at the edge on the inner surface of the inlet opening where the internal surface defining the inlet begins. In other implementations, the textured surface covers the entire internal surface of the inlet proximate the stator blades 161, and no textured surface is present in the inner walls 112 of the housing 110. Still in other implementations, the sintered beaded textured surface can extend along the pump internal walls 112, terminating either on the internal surface proximate to the starting edge of the impeller blades 153, covering the entire internal wall 112 that forms the blood flow path up to the outlet 103, or covering the entire internal wall 112 that forms the flood flow path including the entire internal surface defining the outlet 103. Other implementations may have only the textured surface cover the entire inner surface defining the inlet 101 up to the stator blades 161. Similarly, the textured surface can be located at the inner surface defining the outlet 103, but not having any textured surface on the inner walls 112 of the pump 100a. If an inlet cap is not intended for use in a direct cannulation approach, an external textured surface about the inlet 101 may not be needed unless tissue growth over the external surface is desired.

As discussed above, the shape of the internal wall 112 and the shape of the hub 151 can be configured each individually, or together in combination to create a desired fluid flow pattern and thus adjust pressure recovery within the blood flow path 105 (shown in, e.g., FIG. 3). For example, circumferential blood flow velocity around the hub 151 created by the impeller blades 153 can be reduced by the flared portion 112b of the internal wall 112 without the need for downstream stator blades and without energy losses associated with downstream stator blades. In other words, the effect of the flared portion 112b can include one or both of, for example, reducing circumferential blood flow velocity and limiting energy loss as the blood moves downstream away from the impeller blades 153. As the diameter of the circumferential flow path increases, the circumferential velocity decreases. Flow separation and energy loss associated with flow separation and recirculation can be controlled in part by the shape of the downstream portion 151b of the hub 151. In various respects, flow separation and energy loss are controlled by the shape of the downstream portion 151b relative to the opposing internal wall 112, which can create limited recirculation downstream of the widest portion 151f of the hub 151. In particular, the decrease in the outer diameter of the hub 151 at the end portion 151e may permit a limited amount of recirculation. Some recirculation may be desired to wash the downstream bearing assembly 159, but it may be desired to limit the amount of recirculation to prevent energy loss. Recirculation may be limited such that a greater fluid pressure is achieved at the outlet 103 for a given rotation speed of the rotor 150 without a loss in fluid flow energy.

Figure 6A:
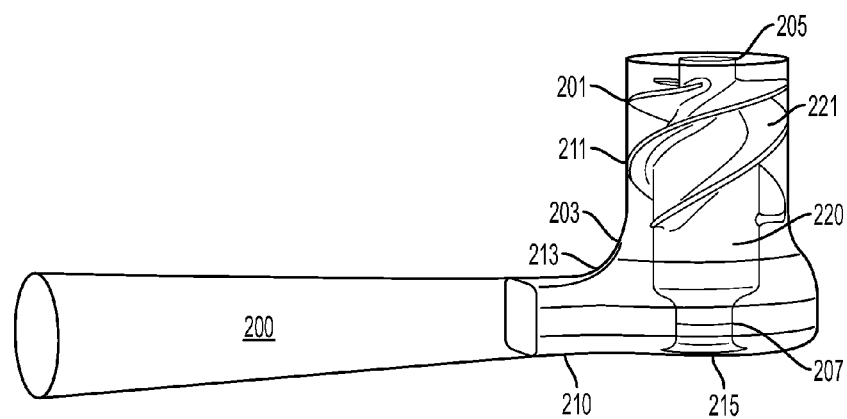
FIGS. 6A-6D are partial cutaway perspective views of alternative blood pump components.

One will appreciate from the description herein that the flow pattern of the blood within the blood flow path 105 can be controlled in a variety of ways using fewer, different, or different combinations of structures. For example, with reference to FIG. 6A, a blood flow path 200 for efficiently converting kinetic energy of blood to static blood pressure is defined by an internal wall 210 of a blood pump housing (not shown). The blood flow path 200 includes an upstream portion 201 having a generally constant width, which is defined by a generally cylindrical portion 211 of the internal wall 210. The upstream portion 201 is configured to receive impeller blades 221 of a rotor 220. Downstream of the blades 221, the blood flow path 200 includes a flared downstream portion 203 having a greater width than the width of the upstream portion 201. The flared downstream portion 203 of the housing is defined by a flared portion 213 of the internal wall 210, which generally has a bell-like shape and includes curvature in two directions, i.e., gradual expansion in an axial direction and radially in a circumferential direction. Unlike the hub 151 discussed above that includes a flared downstream portion 151b, a diameter/width of the rotor 220 may remain generally constant in both the upstream portion 201 and the downstream portion 203. Additionally, and as shown in FIGS. 3 and 4, a width of an upstream bearing assembly 205 at the upstream end can be generally the same as a width of a downstream bearing assembly 207 at the downstream end. In FIG. 6A, both upstream and downstream bearing assemblies 205, 207 have a smaller diameter compared to the diameter/width of the rotor 220. The interior wall 210 includes a generally flat end wall 215 on which a downstream portion of the rotor 220 is supported. Thus, in the implementation illustrated in FIG. 6A, kinetic energy of the blood is converted to fluid pressure by the flared portion 203 of the blood flow path 200. The flared contour of the flared portion 203 extends circumferentially about the rotor 220.

Figure 6B:
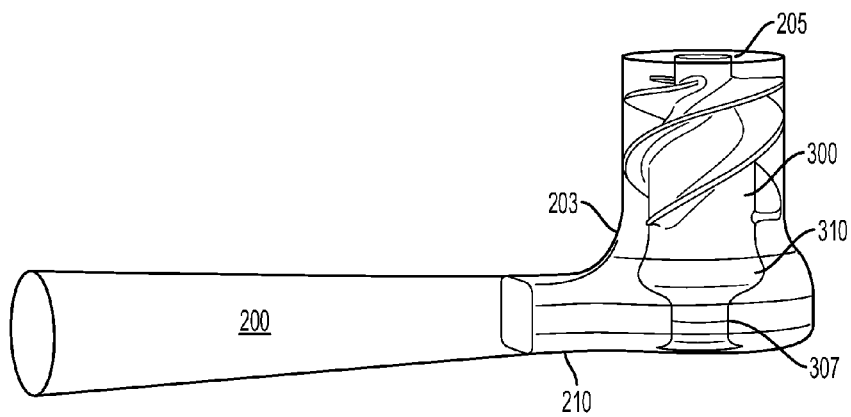

By contrast, as shown in FIG. 6B, a rotor 300, like the rotor 150 of FIGS. 2-4, can include a flared downstream portion 310 that is configured to be disposed proximate the flared downstream portion 203 of the blood flow path 200. The flared downstream portion 310 of the rotor 300 can reduce flow separation and turbulence within the blood flow during use while also increasing the conversion of kinetic energy of the blood to static pressure. Furthermore, by limiting energy losses associated with flow separation, a greater net amount of the kinetic energy of the blood can be converted to static pressure, providing greater energy efficiency for certain flow rates and/or rotation speeds of the rotor 300. Thus, in the implementation of FIG. 6B, the flared portion 203 of the blood flow path 200 and the flared portion 310 of the rotor 300 combine to efficiently convert kinetic energy of the blood to blood pressure. In FIG. 6B, the flared downstream portion 310 of the rotor 300 gradually increases in diameter and then tapers to the diameter of the downstream bearing assembly 307 at the downstream end which is smaller than both the flared portion and the upstream portion of the rotor 300. The upstream bearing assembly 205 at the upstream end and the downstream bearing assembly 307 at the downstream end of as shown in FIG. 6B are similar in diameter and smaller than either the flared downstream portion 310 or the upstream region of the rotor 300.

Figure 6C:
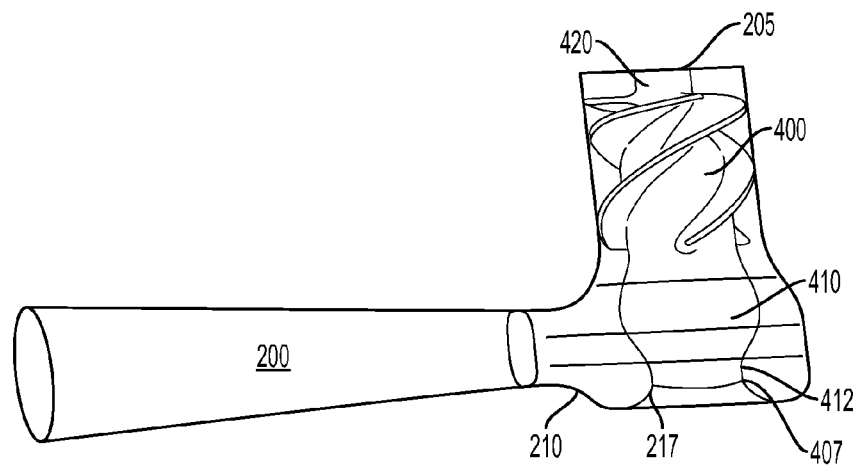

Now referring to FIG. 6C, a downstream portion 410 of a rotor 400 can have an end portion 412 that has a diameter/width greater than an upstream end portion 420 of the rotor 400. The downstream end portion 412 of the rotor 400 can accommodate a downstream bearing assembly 407 that has a greater diameter/width than a diameter/width of an upstream bearing assembly 205 at the upstream end portion 420 of the rotor 400. Furthermore, the downstream bearing assembly 407 can also have a diameter that is greater than the upstream region of rotor hub 400. In other words, the downstream bearing assembly 407 has a smaller diameter relative to the greatest diameter of the flared out portion 410, but a larger diameter relative to each of the upstream bearing assembly 205 and the upstream end portion 420 of the rotor 400. Additionally, the relatively smaller drop in diameter from the flared portion 410 to the larger downstream bearing assembly 407 at the downstream end portion 412 contributes to a desired hydrodynamic effect on blood flow during use. For example, the combination of the flared portion 410 and the downstream bearing assembly 407 (whether of same or larger diameter relative to the upstream bearing assembly 205) can promote recirculation proximate the components of the downstream bearing assembly 407 for washing the downstream bearing components and/or the downstream end portion 410 of the rotor 400 to limit thrombogenesis and to cool the downstream bearing assembly 407.

In general, a transition from flow about a greater diameter to flow about a smaller diameter tends to dissipate energy due to flow separation and recirculation. The amount of energy dissipated in secondary flow patterns within the blood flow path may be affected by several parameters. The amount of energy dissipated can be limited by limiting the diameter difference in transition between the greatest (i.e. maximum) diameter of the rotor 400 and the diameter of the downstream bearing assembly 407. Thus a downstream bearing assembly 407 that is larger than the upstream bearing assembly 205 and approximates (but is smaller than) the diameter of the flared portion 410 of the rotor 400 increases efficiency of blood flowing downstream, contributing to a higher efficiency of the pump while promoting recirculation. In addition, the difference in diameter between the greatest diameter of the rotor 400 and the diameter of the downstream bearing assembly 407 can be selected to cause a desired amount of recirculation at the downstream bearing assembly 407 in order to wash the downstream bearing assembly 407. The amount of energy dissipated may also be affected by the size of the gap between the rotor 400 and the internal wall as further described below.

The internal wall 210 can include a contoured end wall 217 to control blood flow proximate the downstream bearing and the contoured end wall 217. For example, the contoured end wall 217 can turn the blood flow from an axial direction to a radial direction to guide the blood to the outlet with reduced energy loss. The downstream bearing can also have a width that does not present a reduction in the diameter at a transition from the contoured end wall 217 such that energy losses due to flow separation are generally prevented or limited while maintaining bearing washing. Additionally, since the axial velocity of the blood tends to account for less of the kinetic energy of the blood than the circumferential velocity, energy losses associated with redirecting the blood are relatively small.

Figure 6D:
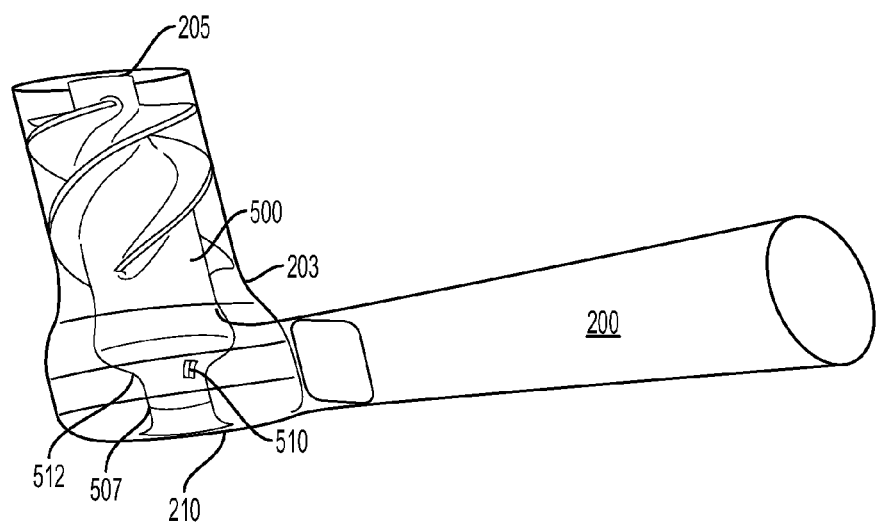

As shown in FIG. 6D, a rotor 500 can also include one or more mixing blades 510 to limit thrombogenesis and/or recirculation downstream of the flared portion 203 of the blood flow path 200. For example, a shape of the rotor 500 that efficiently converts kinetic energy of the blood to static pressure may cause a persistent recirculation zone (not shown) proximate a downstream bearing assembly 507. To improve bearing cooling and to limit formation of blood clots or other blood damage, a mixing blade 510 can be included proximate the downstream bearing assembly 507 to enhance blood recirculation and washing of the downstream bearing assembly 507. The mixing blade can be disposed on a tapered portion of the rotor 500, for example, a tapered portion 512 that has an outer diameter that decreases in a downstream direction. Mixing blades 510 can be applied to all combinations of various impeller blade configurations, rotor hub configurations, and different bearing assembly sizes described above and below.

Figure 7:
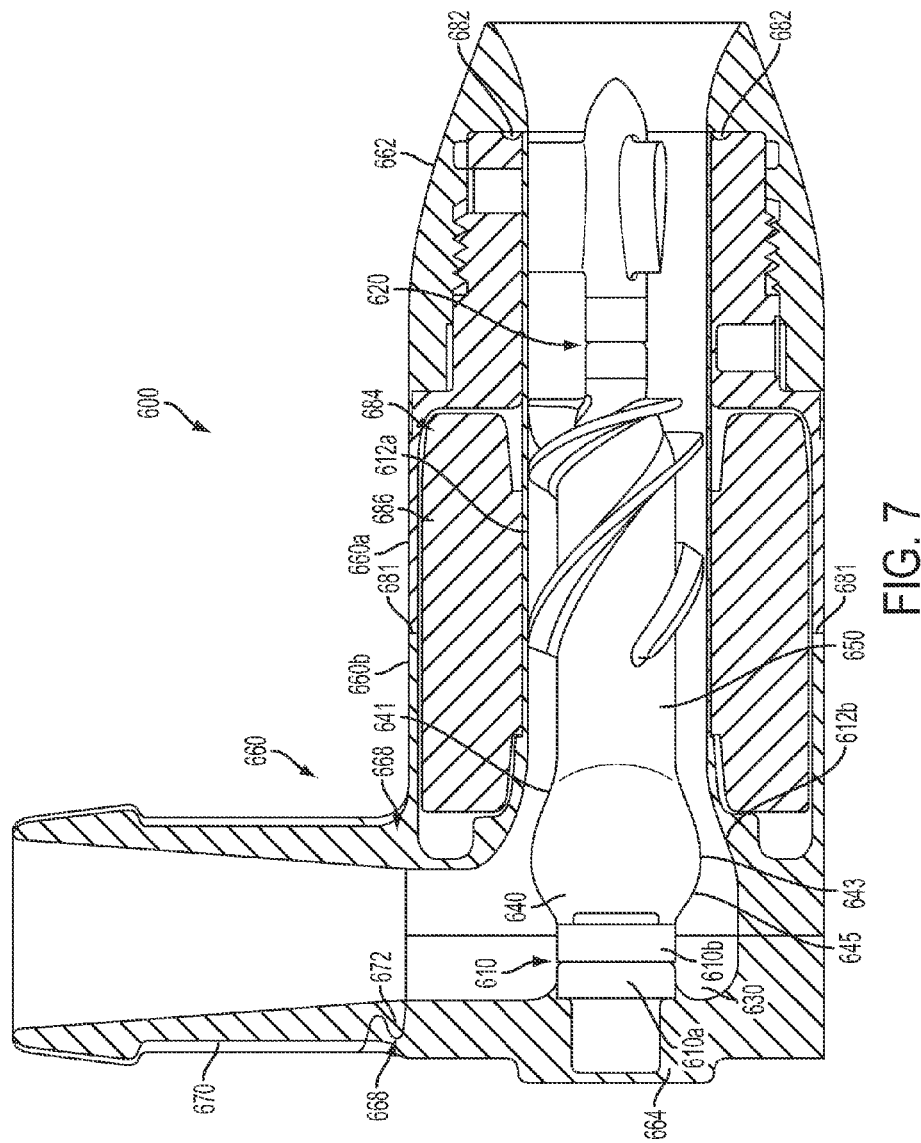
FIG. 7 is a partial cross-sectional view of an alternative blood pump.
Figure 8:
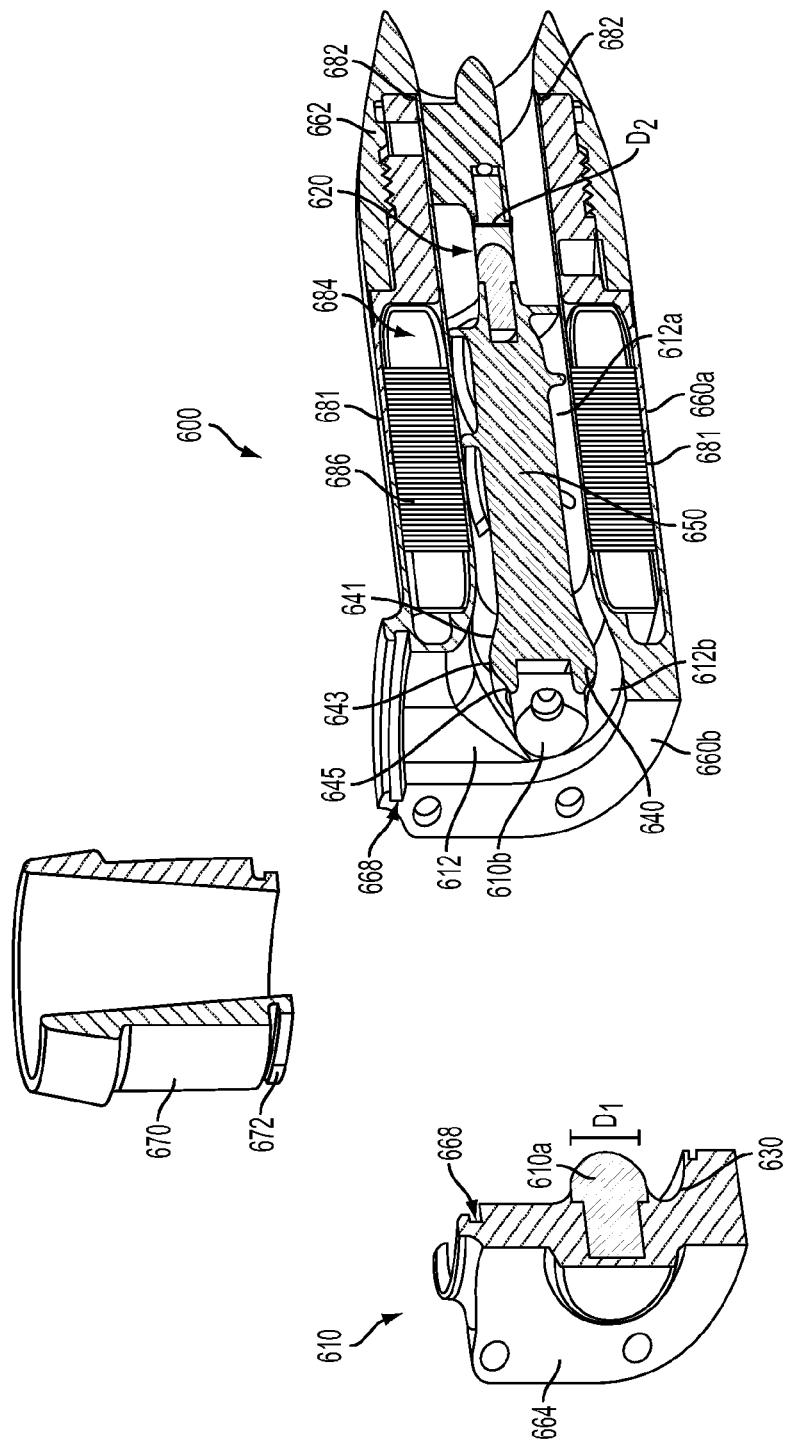
FIG. 8 is an exploded partial cross-sectional view of the blood pump of FIG. 7.

Now referring to FIGS. 7 and 8, an alternative blood pump 600 includes a downstream bearing 610 that includes a ball component 610a and a cup component 610b. The downstream bearing 610 has a diameter $D_1$ greater than a diameter $D_2$ of the upstream bearing 620 (FIG. 8). The blood pump 600 also includes a contoured end wall 630. As shown, a rounded or flared downstream portion 640 of the rotor 650 includes a rounded leading surface 641 upstream of a widest portion 643 and a rounded trailing surface 645 downstream of the widest portion 643. The rounded leading surface 641 has an outer contour that increases in the downstream direction and generally matches a contour of a flared portion 612b of an internal wall 612. As a result, a gap between the rotor 650 and the internal flared portion 612b remains approximately the same as a gap between the rotor 650 and an inner portion 612a that is generally cylindrical. The rounded trailing surface 645 has a contour that decreases in the downstream direction between the widest portion 643 of the rotor 650 and the cup component 610b.

The blood pump 600 includes a housing 660 that includes two body components 660a, 660b, an inlet cap 662, and end cap 664. The body component 660b includes the generally cylindrical inner portion 612a, which defines the flow path about the rotor 650. The two body components, 660a, 660b, forming an upstream portion and a downstream portion respectively, are secured by circumferential welds 681, 682, with one weld 681 located about the exterior of the blood pump 600, and another weld 682 located near the inlet of the blood pump 600. Together, the upstream and downstream body components 660a, 660b define a generally cylindrical compartment 684 that houses a motor stator 686. The cylindrical inner portion 612a of the body component 660b extends across the entire inner portion of the compartment 684. During assembly of the pump 600, the motor stator 686 can slide over the cylindrical inner portion 612a, after which the body component 660a can slide over the cylindrical inner portion 612a. In the assembled pump 600, on the exterior of the housing 660, a portion of the body component 660b extends about the motor stator 686, and a portion of the body component 660a extends about the motor stator 686. The weld 681 between the body components 660a, 660b can be located, for example, approximately halfway along the length of the compartment 684, such that each of the body components covers approximately half of the motor stator 686.

The inlet cap 662 threadedly attaches to the upstream body component 660a, and an end cap 664 is attached to the downstream body component 660b with welds and/or screws. The housing 660 also includes an outflow conduit portion 670 coupled between the end cap 664 and the body component 660b. The end cap 664 and the body component 660b define channels 668, which receive a circumferential ridge 672 located about the outflow conduit portion 670 to secure the outflow conduit portion 670.

In contrast with other axial flow pumps that rely on physical structural bearings for rotor suspension, the pump implementations in this disclosure do not require stator blades downstream relative to the rotor 650. Furthermore, while other axial flow pumps have physical bearings at a location in the middle of a path of blood that flows axially from up to down-stream, the downstream bearing assembly 610 of the blood pump 600 is on an end of the blood pump 600. The blood flows at an angle transversely away from the path of blood flowing from upstream, not axially away from the downstream bearing assembly 610. Furthermore, as shown in FIG. 7, the pump outlet initially has a relatively constant diameter but gradually increases radially outward, relative to the flow path, towards the tip of the outlet.

Figure 9:
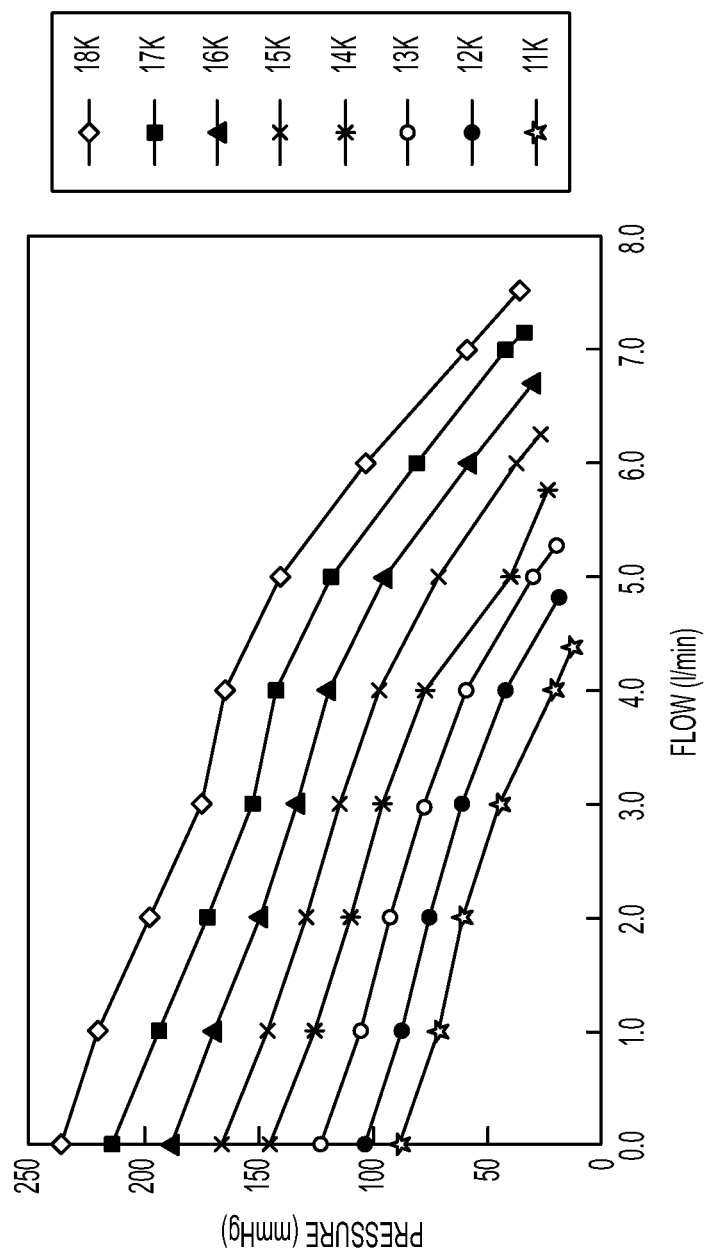
FIG. 9 is a chart that illustrates an example of flow characteristics of a blood pump.

Referring to FIG. 9, a chart shows examples of flow characteristics for a blood pump. Curves indicating flow rates of a blood analog vs. outflow pressures are illustrated for different rotor speeds, illustrating results that are achievable with some implementations of the techniques described above. Pump efficiency and flow characteristics can vary from one implementation to another, and thus the techniques described herein can be implemented so that different results are achieved. For the particular pump configuration for the example of FIG. 9, flow rates in excess of 7.0 lpm were achieved, and output pressures of over 200 mmHg were achieved. A flow rate of approximately 5.0 lpm was achieved at about 16,000 rpm and an outlet pressure of about 100 mmHg. Under these conditions, the pump exhibited improved efficiency over comparison pumps, indicated by lower power consumption at similar flow rates and output pressures.

Figure 10:
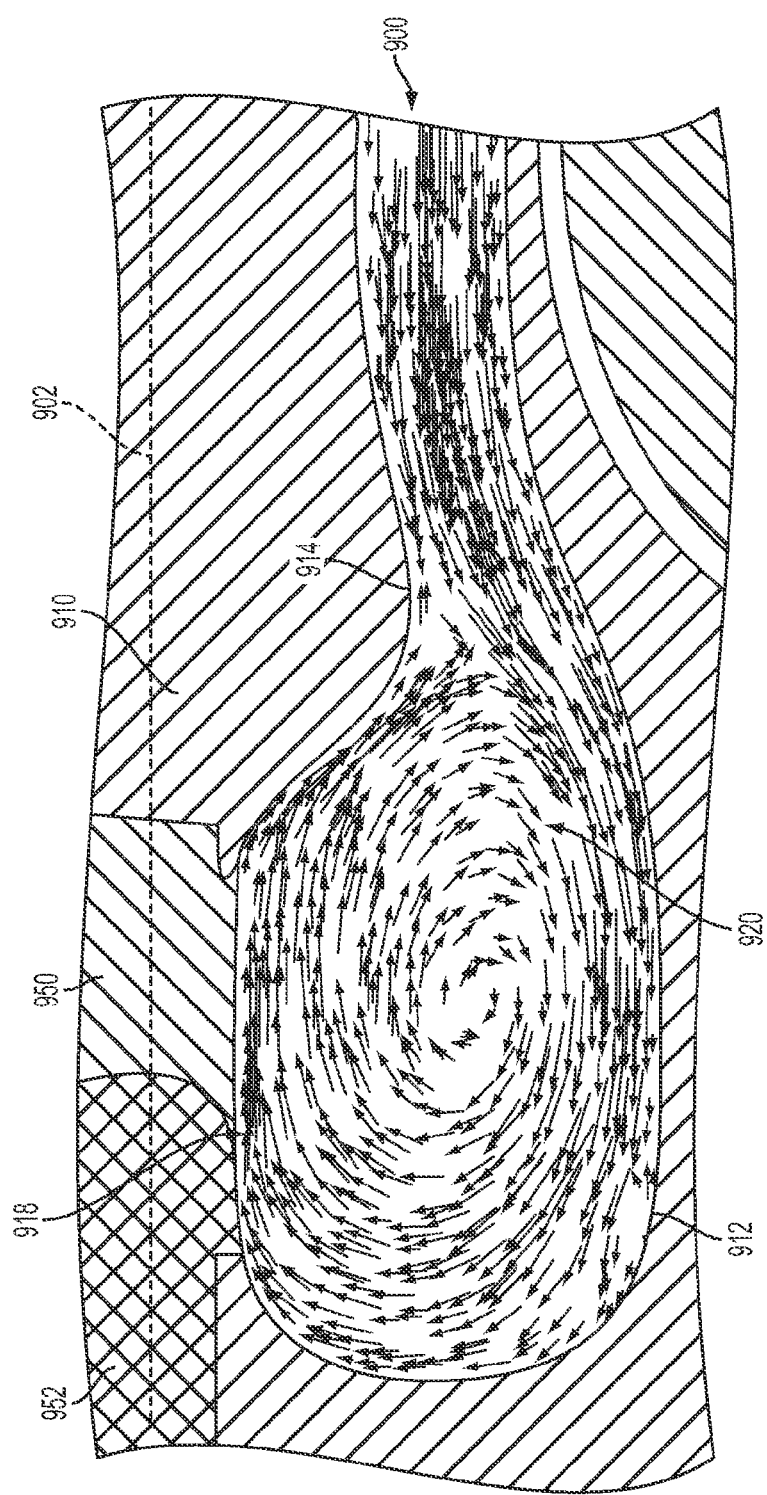
FIG. 10 is a diagram that illustrates an example of a fluid flow in a blood pump.

FIG. 10 illustrates a downstream flow pattern 900 of a blood pump. The flow pattern 900 illustrates blood flow proximate a hub 910 of the blood pump, including flow downstream of a flared portion of the hub 910. This figure represents a cross-sectional view of the flow pattern at the downstream region of the pump, observed opposite the side with the outflow cannula. A midline 902 represents the line that splits the pump into the two halves, for example, the axis of rotation of a rotor. An inner wall 912 of the housing and an outer contour 914 of the hub 910 of the rotor are shown. The blood flow pattern 900, as observed in the flow path, includes limited recirculation. At a location 918 adjacent downstream bearing components 950, 952 of the blood pump, recirculation is permitted to wash the bearing components 950, 952. Recirculation can occur in a substantially regular pattern 920, limiting energy dissipation in the recirculating flow.

Figure 11:
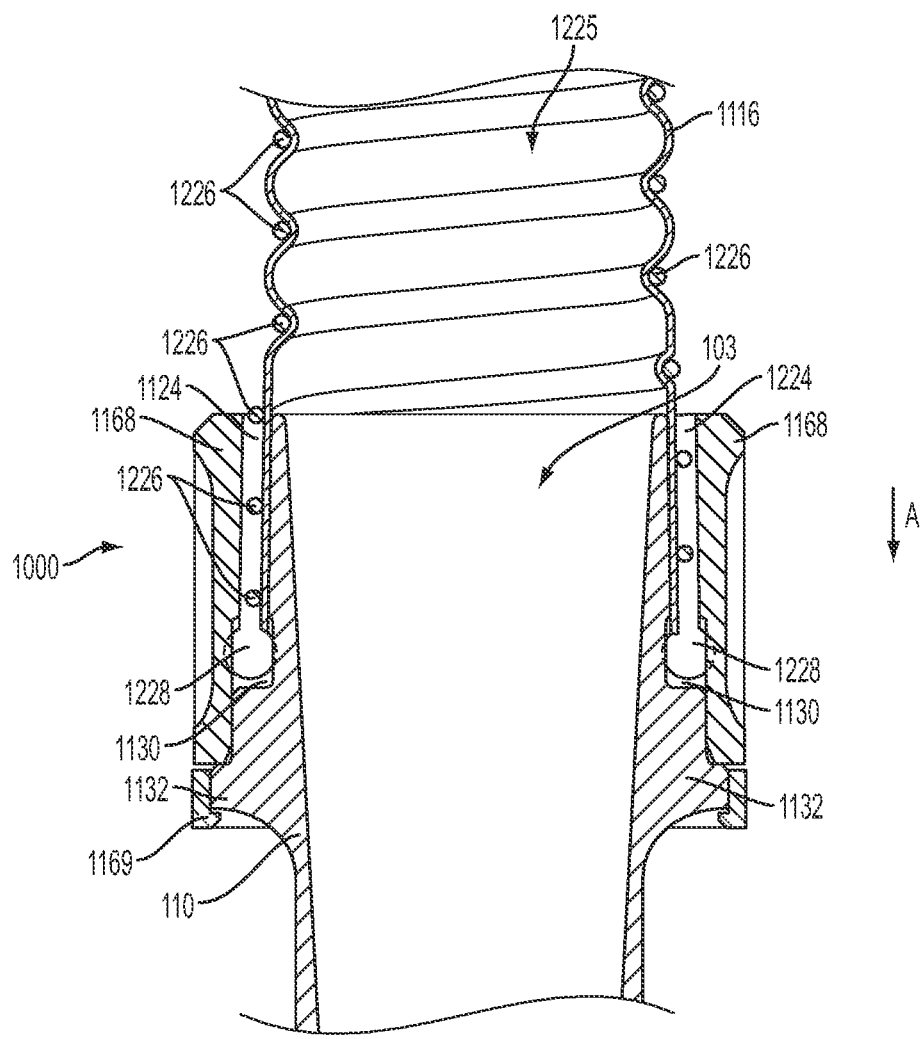
FIG. 11 is a cross-sectional view of a graft assembly.

FIG. 11 illustrates an exemplary graft assembly 1000 for use with a blood pump, such as the blood pump 100a. The exemplary graft assembly 1000 provides fluid communication from the outlet 103 of the pump 100a to a target vasculature, vessel, or organ in the circulatory system. The graft assembly 1000 includes a conduit 1116 that defines a lumen 1225, a reinforcement component 1226 about the conduit 1116, and a support structure 1224 molded about the conduit 1116.

The conduit 1116 can be formed of, for example, a woven material, for permitting the conduit 1116 to be sewn to, for example, a blood vessel. The material of the conduit can be a non-synthetic or synthetic material, including, but not limited to PTFE and Dacron. The reinforcement component 1226, such as a wire, is helically wrapped about the conduit 1116 to provide the conduit 1116 with additional strength and to prevent kinking of the conduit when in use. The conduit 1116 has inherent resiliency such that it can maintain its shape after twisting or being subjected to a compression force. Preferably, every point along the conduit 1116 can incorporate a slightly elastic or resilient property to resist kinking or compression. The support structure 1224 is molded about an end region of the conduit 1116. The support structure 1224 may be rigid or flexible, but it is designed to anchor the conduit 1116 over the external housing of the pump 100a or at the outlet 103 of the pump 100a. The wire reinforcement component 1226 can be embedded within the support structure 1224. The support structure 1224 has a lip or a flange 1228 at an end that extends about the conduit 1116 and laterally inward and outward from the conduit 1116 to provide anchoring.

In some implementations, the graft assembly 1000 can engage exterior housing features of the pump 100a to attach and seal around the outlet 103. Proximate the outlet 103, the exterior of the housing 110 includes a recessed portion 1130 and a raised portion 1132 that extend partially or completely about the outlet 103. The conduit 1116 can slide over the outlet 103 in the direction of arrow A until the flange 228 reaches the recessed portion 1130 and the support structure 1224 engages the raised portion 1132, limiting further motion toward the pump 100a. To secure the conduit 1116 to the housing 110, the fitting 1168 can be, for example, pulled over the molded support structure 1224 in the direction of arrow A such that a portion 1169 of the fitting 1168 snaps over and couples with the raised portion 1132 about the outlet 103. As the fitting 1168 slides over the support structure 1224, the fitting 1168 compresses the flange 1228 into the recessed portion 1130, forming a seal around the outlet 103.

In some implementations, an inner portion of the fitting 1168 can be threaded to engage external threads (not shown) of the housing 110 that are located about the outlet 103. Screwing the fitting over the support structure 1224 and the external threads compresses the flange 1228 to form a seal about the outlet 103. In some implementations, the fitting 1168 is formed of two semi-cylindrical pieces that fit over the conduit 1116 and a portion of the housing 110 to capture the support structure 1224 and compress the flange 1228 to form a seal. The two semi-cylindrical pieces can attach to each other via, for example, set screws.

In some implementations, a diameter of the lumen 1225 is the same as a diameter at the opening of the outlet 103. Generally, the lumen 1225 has the same diameter as the opening of the outlet 103. Thus the outflow blood path has generally consistent diameter between a region proximate the downstream bearing assembly 159 through the conduit 1116. The conduit 1116 can additionally or alternatively have a funnel or tapered lumen 1225 if the opening at the outlet 103 has a larger diameter that the region proximate the downstream bearing assembly 159.

When the various configurations of blood pumps described above are used, and as mentioned above, the rotor of a blood pump is driven to impart kinetic energy to the blood within a blood flow path. To provide efficient transfer of kinetic energy to the blood while limiting or preventing damage to the blood, the impeller blades of the rotor are configured to impart a substantial circumferential component of the velocity of the blood in addition to an axial velocity component. Additionally, the rotor and the pump housing are configured to create generally smooth flow over the rotor to limit energy losses associated with flow separation.

As the blood flows in the direction of the axis of rotation of the rotor downstream of the rotor blades, the blood is directed by the shape of the blood flow path to a portion of the blood flow path where the kinetic energy of the blood, including the circumferential velocity component of the blood flow, is converted to blood pressure to cause blood to flow from the pump into the patient's circulatory system and through the patient's circulatory system. For example, the size of the blood flow path between the rotor and the housing is generally maintained constant while the area of the blood flow path is increased such that the velocity of the blood is reduced. Additionally, circumferential blood flow is at least partially converted to radial blood flow as the circumference of the rotor and the housing increases in the downstream portion of the blood flow path.

Recirculation within the blood flow is limited by the shape of the downstream end of the rotor and the shape and size of the downstream bearing component that supports the downstream end of the rotor. Particularly, the rotor is configured to create a desired amount of flow separation and a secondary recirculation flow pattern near the downstream bearing to wash the downstream bearing and the downstream end of the rotor. More than the desired amount of flow separation and recirculation is prevented by a contoured downstream end of the rotor and a downstream bearing that has a greater width than the upstream portion of the rotor or an upstream bearing, at least at a portion of the downstream bearing that is exposed to the blood flow.

The blood flow is then directed by the shape of the housing toward an outlet of the housing. Any remaining axial flow velocity component is converted to a radial flow velocity by the housing, such as at an end wall surrounding the downstream bearing, such that the blood flows out the outlet cannula.

A number of implementations have been described. Nevertheless, it will be understood that various modifications may be made without departing from the spirit and scope of the claimed invention. For example, different configurations of impeller blades, bearing styles, and motors can be used. Similarly, different assemblies can be used to produce the same or similar blood pumps. Implementations can include any appropriate combination or subcombination of features described above. For example, some of or all of the features described for the blood pumps 100a, 600 can be combined or implemented individually.

Accordingly, other embodiments are within the scope of the following claims.

The invention claimed is:

1. A blood pump comprising:
  a hub having an axis of rotation and a midpoint, the hub further having a generally cylindrical upstream portion that is upstream of the midpoint and a downstream portion arranged along the axis of rotation of the hub and downstream of the midpoint, the hub including a magnetic material; and
  blades disposed on the generally cylindrical upstream portion of the hub;
  at least a portion of the downstream portion of the hub having an outer dimension that increases in a downstream direction; and
  wherein the blades are only disposed upstream of the downstream portion of the hub.

2. The blood pump of claim 1, further comprising an upstream bearing component carried on the upstream portion of the hub and a downstream bearing component carried on the downstream portion of the hub, the downstream bearing component having a maximum outer diameter greater than a maximum outer diameter of the upstream bearing component.

3. The blood pump of claim 1, wherein the downstream portion of the hub has a tapered downstream end.

4. The blood pump of claim 3, wherein the tapered downstream end has a rounded surface.

5. The blood pump of claim 3, further comprising a mixing element on the tapered downstream end, the mixing element being configured to rotate with the hub.

6. The blood pump of claim 1, further comprising:
  a housing defining an inlet, an outlet, and a flow path from the inlet to the outlet; and
  a motor stator disposed within the housing.

7. The blood pump of claim 6, wherein the housing includes an internal wall defining the flow path, the internal wall having a width proximate the downstream portion of the hub that is greater than a width of the internal wall proximate the upstream portion of the hub.

8. The blood pump of claim 1, wherein the downstream portion has a rounded surface, and wherein along the rounded surface, an outer diameter of the hub increases in a downstream direction to a maximum outer diameter of the hub and the outer diameter decreases in a downstream direction from the maximum outer diameter.

9. The blood pump of claim 1, wherein the blades extend axially along at least a portion of the magnetic material in the hub.

10. The blood pump of claim 1, wherein the blades terminate at or upstream of the midpoint along a length of the rotor.

11. The blood pump of claim 1, further comprising a housing having an internal wall for housing the hub, wherein a portion of the internal wall is oriented orthogonal to the axis of rotation; wherein the downstream portion of the hub that is downstream of the midpoint is supported within the housing by a downstream bearing assembly; and wherein the downstream bearing assembly couples directly with the portion of the internal wall that is oriented orthogonal to the axis of rotation.

12. The blood pump of claim 1, further comprising stator blades disposed only upstream of the downstream portion of the hub.

13. A blood pump, comprising:
a housing, the housing having an internal wall defining an inlet, an outlet, and a flow path from the inlet to the outlet; the flow path having a generally cylindrical volume proximate the inlet, and a flared volume located downstream of the generally cylindrical volume, the generally cylindrical volume having a first width and the flared volume having an increasing width greater than the first width;
a motor stator disposed within the housing; and
a motor rotor disposed within the flow path, the motor rotor having a hub, an axis of rotation of the hub, blades for pumping blood, a midpoint, and a magnetic material for electromagnetic rotation of the motor rotor,
wherein the flared volume expands radially outward from the axis of rotation downstream from the midpoint of the motor rotor and a portion of the hub that is downstream of the midpoint is disposed within the flared volume, and
wherein at least a portion of the generally cylindrical volume is located between the motor stator and the motor rotor; and
stator blades disposed only upstream of the downstream portion of the hub.

14. The blood pump of claim 13, wherein the hub includes a generally cylindrical upstream portion and a flared downstream portion, the flared downstream portion having a width greater than a width of the generally cylindrical upstream portion, and
wherein the motor stator extends about the generally cylindrical upstream portion of the hub.

15. The blood pump of claim 14, wherein the flared downstream portion of the hub flares outward from the axis of rotation of the hub, and at least a portion of the flared downstream portion of the hub is circumferentially surrounded by the flared volume.

16. The blood pump of claim 14, further comprising a downstream bearing having a first bearing component mounted in the internal wall and a second bearing component carried by the flared downstream portion of the hub.

17. The blood pump of claim 16, wherein the internal wall includes a contoured portion proximate the first bearing component.

18. The blood pump of claim 16, further comprising an upstream bearing having a third bearing component carried by an upstream end portion of the hub and a fourth bearing component carried by a bearing stator disposed within the flow path.

19. The blood pump of claim 18, wherein a position of the bearing stator along the axis of rotation is variable.

20. The blood pump of claim 13, wherein the motor stator extends around the internal wall.

21. The blood pump of claim 13, wherein the motor stator is located outside the flow path.

22. The blood pump of claim 13, wherein the motor stator extends around portions of the blades.

23. The blood pump of claim 15, wherein the flared downstream portion of the hub and the flared volume are located downstream of the blades.

24. The blood pump of claim 13, wherein the blades of the hub terminate at or before the midpoint along a length of the rotor.

25. The blood pump of claim 13, wherein a portion of the internal wall is oriented orthogonal to the axis of rotation; wherein a downstream portion of the rotor that is downstream of the midpoint is supported within the flow path by a downstream bearing assembly; and wherein the downstream bearing assembly couples directly with the portion of the internal wall that is oriented orthogonal to the axis of rotation.

26. A method for pumping blood comprising:
imparting kinetic energy to blood within a first portion of a blood flow path to increase blood flow velocity in the blood flow path, the blood flow path defined by a rotor hub and a wall;
directing the blood to a second portion of the blood flow path that circumferentially surrounds a downstream portion of the rotor hub that is downstream from a midpoint of the rotor hub, the second portion of the blood flow path having an outer dimension that increases in a downstream direction, the second portion having a greater width than a width of the first portion of the blood flow path; and
converting at least a portion of the kinetic energy of the blood to fluid pressure in the second portion of the blood flow path; and
stator blades disposed only upstream of the downstream portion of the hub.

27. The method of claim 26, further comprising limiting separation of the blood flow from a surface of the rotor hub in the second portion of the blood flow path.

28. The method of claim 26, further comprising reducing recirculation within the blood flow downstream of the second portion of the blood flow path.

29. The method of claim 26, wherein imparting kinetic energy comprises increasing an axial velocity and/or a circumferential velocity of the blood within the first portion of the blood flow path.

30. The method of claim 26, wherein directing the blood to the second portion of the blood flow path comprises directing the blood to a second portion of the blood flow path that has a diameter that expands in a downstream direction, the second portion circumferentially surrounding a portion of the rotor hub that has an outer diameter that increases in a downstream direction.

31. The method of claim 26, wherein the rotor hub comprises impeller blades and wherein the impeller blades terminate at or before the midpoint along a length of the rotor hub.

32. The method of claim 26, wherein a portion of the wall is oriented orthogonal to an axis of rotation of the rotor hub; wherein the downstream portion of the rotor hub that is downstream of the midpoint is supported within the blood flow path by a downstream bearing assembly; and wherein the downstream bearing assembly couples directly with the portion of the wall that is oriented orthogonal to the axis of rotation such that no blood flows in an axial direction downstream of the downstream bearing assembly.

33. A blood pump comprising:
a rotor having blades configured to generate a circumferential flow and a downstream portion located downstream of a midpoint of the rotor, the downstream portion having an outer diameter that expands in a downstream direction to decrease a circumferential velocity of the circumferential flow; and
a housing defining a flow path, the housing being configured to convert the circumferential flow to fluid pressure at an outlet; and
stator blades disposed only upstream of the downstream portion of the motor rotor.

34. The blood pump of claim 33, wherein the housing is configured to convert the circumferential flow to fluid pressure without stator blades located downstream of the blades of the rotor.

35. The blood pump of claim 33, wherein the downstream portion is dimensioned to decrease the circumferential flow along an axis of rotation of the rotor, the downstream portion being located on the rotor downstream of the blades.

36. The blood pump of claim 33, wherein the downstream portion includes a flared portion having a cross-sectional dimension that increases along a downstream dimension.

37. The blood pump of claim 36, wherein the housing includes a flared portion located about the flared portion of the rotor, such that an inner cross-sectional dimension of the housing increases along the downstream dimension.

38. The blood pump of claim 33, wherein the outer diameter of the downstream portion expands to a maximum outer diameter of the hub.

39. The blood pump of claim 33, wherein the blades terminate at or before the midpoint along a length of the rotor.

40. The blood pump of claim 33, wherein a portion of the housing is oriented orthogonal to an axis of rotation of the rotor; wherein the downstream portion of the rotor that is downstream of the midpoint is supported within the housing by a downstream bearing assembly; and wherein the downstream bearing assembly couples directly with the portion of the housing that is oriented orthogonal to the axis of rotation such that no blood flows in an axial direction downstream of the downstream bearing assembly.

41. A blood pump comprising:
a housing defining an inlet, an outlet, and a flow path between the inlet and the outlet, the housing having an exterior wall and an internal wall, the interior wall defining the flow path;
a motor stator located between the internal wall and the external wall; and
a rotor mechanically suspended in the housing and located within the flow path, the rotor having an axis of rotation and blades configured to produce an axial flow about the rotor along the axis of rotation,
the housing being configured to direct the axial flow to the outlet in a direction off the axis of rotation; and
stator blades disposed only upstream of the downstream portion of the motor rotor.

42. The blood pump of claim 41, wherein the housing is configured to direct the axial flow to the outlet in a direction generally perpendicular to the axis of rotation.

43. The blood pump of claim 41, wherein the blades terminate at or before a midpoint along a length of the rotor.

44. The blood pump of claim 41, wherein a portion of the internal wall is oriented orthogonal to the axis of rotation; wherein a downstream portion of the rotor that is downstream of the midpoint is supported within the flow path by a downstream bearing assembly; and wherein the downstream bearing assembly couples directly with the portion of the internal wall that is oriented orthogonal to the axis of rotation such that no blood flows in an axial direction downstream of the downstream bearing assembly.

* * * * *